United States Patent
Dubal

(10) Patent No.: US 10,632,180 B2
(45) Date of Patent: Apr. 28, 2020

(54) METHODS AND COMPOSITIONS FOR IMPROVED COGNITION

(71) Applicant: The Regents of the University of California, Oakland, CA (US)

(72) Inventor: Dena Dubal, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/548,306

(22) PCT Filed: Feb. 5, 2016

(86) PCT No.: PCT/US2016/016842
§ 371 (c)(1),
(2) Date: Aug. 2, 2017

(87) PCT Pub. No.: WO2016/127097
PCT Pub. Date: Aug. 11, 2016

(65) Prior Publication Data
US 2018/0015151 A1    Jan. 18, 2018

Related U.S. Application Data

(60) Provisional application No. 62/113,300, filed on Feb. 6, 2015.

(51) Int. Cl.
*A61K 38/47* (2006.01)
*C12N 9/24* (2006.01)
*A61P 25/28* (2006.01)
*A61K 38/00* (2006.01)

(52) U.S. Cl.
CPC .............. *A61K 38/47* (2013.01); *A61P 25/28* (2018.01); *C12N 9/2402* (2013.01); *C12Y 302/01031* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 6,579,850 B1 † | 6/2003 | Nabeshima | |
| 8,420,088 B2 | 4/2013 | Glass et al. | |
| 8,481,031 B2 † | 7/2013 | Glass | |
| 8,778,887 B2 † | 7/2014 | Breyer | |
| 2011/0195077 A1 | 8/2011 | Glass et al. | |
| 2012/0172314 A1 † | 7/2012 | Koeffler | |
| 2018/0037623 A1 | 2/2018 | Guo et al. | |

FOREIGN PATENT DOCUMENTS

| | | |
|---|---|---|
| EP | 1374877 A1 | 1/2004 |
| EP | 2247614 B1 | 4/2014 |
| JP | 2006240990 A | 9/2006 |
| WO | 2004100976 A1 | 11/2004 |
| WO | 2017/085317 A1 | 5/2017 |

OTHER PUBLICATIONS

Xu et al. ("Molecular Basis of Klotho" From Gene to Function in Aging Endocr Rev Apr. 2015 36(2):174-193).*
Dubal et al., "Life Extension Factor Klotho Enhances Cognition," Cell Reports, May 22, 2014, vol. 7, No. 4, 1065-1076.
Foster, "Biological Markers of Age-Related Memory Deficits," CNS Drugs, 2006, vol. 20, No. 2, 153-166.
Lennart, "Neurobiology and Therapeutic Potential of Klotho," http://grantome.com/grant/NIH/R01-NS088532-01, 2014.
Abraham, et al. "Small-molecule Klotho enhancers as novel treatment of neurodegeneration." Future medicinal chemistry 4, No. 13 (2012): 1671-1679.
Arking, et al. "Association of human aging with a functional variant of klotho." Proceedings of the National Academy of Sciences 99, No. 2 (2002): 856-861.
Chang, et al. "The β-glucuronidase klotho hydrolyzes and activates the TRPV5 channel." Science 310, No. 5747 (2005): 490-493.
Château, et al. "Klotho interferes with a novel FGF-signalling pathway and insulin/Igf-like signalling to improve longevity and stress resistance in Caenorhabditis elegans." Aging (Albany NY) 2, No. 9 (2010): 567.
Chen, et al. "Inhibition of lung cancer cells growth, motility and induction of apoptosis by Klotho, a novel secreted Wnt antagonist, in a dose-dependent manner." Cancer biology & therapy 13, No. 12 (2012): 1221-1228.
Chen, et al. "The antiaging protein Klotho enhances oligodendrocyte maturation and myelination of the CNS." Journal of Neuroscience 33, No. 5 (2013): 1927-1939.
Dubal, et al. "Life extension factor klotho prevents mortality and enhances cognition in hAPP transgenic mice." Journal of Neuroscience 35, No. 6 (2015): 2358-2371.
Duce, et al., "Gene profile analysis implicates Klotho as an important contributor to aging changes in brain white matter of the rhesus monkey." Glia 56, No. 1 (2008): 106-117.
Imura, et al. "Secreted Klotho protein in sera and CSF: implication for post-translational cleavage in release of Klotho protein from cell membrane." FEBS letters 565, No. 1-3 (2004): 143-147.
Imura, et al. "α-Klotho as a regulator of calcium homeostasis." Science 316, No. 5831 (2007): 1615-1618.
Invidia, et al. "The frequency of Klotho KL-VS polymorphism in a large Italian population, from young subjects to centenarians, suggests the presence of specific time windows for its effect." Biogerontology 11, No. 1 (2010): 67.
Kuang, et al. "Klotho upregulation contributes to the neuroprotection of ligustilide in an Alzheimer's disease mouse model." Neurobiology of aging 35, No. 1 (2014): 169-178.

(Continued)

*Primary Examiner* — James H Alstrum-Acevedo
*Assistant Examiner* — Tara L Martinez
(74) *Attorney, Agent, or Firm* — Kilpatrick Townsend & Stockton LLP

(57) ABSTRACT

Provided herein are klotho polypeptide compositions and methods for improving cognitive function in an individual comprising treatment of with klotho polypeptides.

21 Claims, 7 Drawing Sheets
Specification includes a Sequence Listing.

(56) References Cited

OTHER PUBLICATIONS

Kurd-O, et al. "Mutation of the mouse klotho gene leads to a syndrome resembling ageing." nature 390, No. 6655 (1997): 45.
Kurosu, et al. "Suppression of aging in mice by the hormone Klotho." Science 309, No. 5742 (2005): 1829-1833.
Liu, et al. "Augmented Wnt signaling in a mammalian model of accelerated aging." Science 317, No. 5839 (2007): 803-806.
Nagai, et al. "Cognition impairment in the genetic model of aging klotho gene mutant mice: a role of oxidative stress." The FASEB Journal 17, No. 1 (2003): 50-52.
Razzaque, "The FGF23-Klotho axis: endocrine regulation of phosphate homeostasis." Nature Reviews Endocrinology 5, No. 11 (2009): 611.
Semba, et al. "Plasma klotho and mortality risk in older community-dwelling adults." Journals of Gerontology Series A: Biomedical Sciences and Medical Sciences 66, No. 7 (2011): 794-800.
Semba, et al. "Klotho in the cerebrospinal fluid of adults with and without Alzheimer's disease." Neuroscience letters 558 (2014): 37-40.
Shiozaki, et al. "Morphological and biochemical signs of age-related neurodegenerative changes in klotho mutant mice." Neuroscience 152, No. 4 (2008): 924-941.
Shiraki-Iida, et al. "Structure of the mouse klotho gene and its two transcripts encoding membrane and secreted protein." FEBS letters 424, No. 1-2 (1998): 6-10.
Tohyama, et al. "Klotho is a novel β-glucuronidase capable of hydrolyzing steroid β-glucuronides." Journal of Biological Chemistry 279, No. 11 (2004): 9777-9784.
Touré, et al. "The role of the acidity of N-heteroaryl sulfonamides as inhibitors of Bcl-2 family protein-protein interactions." ACS medicinal chemistry letters 4, No. 2 (2013): 186-190.
Tucker Zhou,et al. "Biochemical and functional characterization of the klotho-VS polymorphism implicated in aging and disease risk." Journal of Biological Chemistry 288, No. 51 (2013): 36302-36311.
Urakawa, et al. "Klotho converts canonical FGF receptor into a specific receptor for FGF23." Nature 444, No. 7120 (2006): 770.
Wang, et al. "Current understanding of klotho." Ageing research reviews 8, No. 1 (2009): 43-51.
Yokoyama, et al. "Variation in longevity gene Klotho is associated with greater cortical volumes." Annals of clinical and translational neurology 2, No. 3 (2015): 215-230.
"BU Researchers Discover that Klotho is Neuroprotective Against Alzheimer's Disease Toxic Amyloid," Jul. 28, 2014, accessed at https://www.bu.edu/news/2014/07/28/bu-researchers-discover-that-klotho-is-neuroprotective-against-alzheimers-disease-toxic-amyloid/.
"Genes and Intelligence: The 3% Solution," The Economist, May 8, 2014, accessed at https://www.economist.com/science-and-technology/2014/05/08/the-3-solution.
Database WPI Week 201041, Thomas Scientific, London, GB AN 2012-G56327, XP002783543, pp. 1-2, and CN 101 711 779 a (Univ Cent South) May 10, 2010.
Database WPI Week 201271, Thomas Scientific, London, GB AN 2012-M64840, XP002783542, pp. 1-2, and JP 2012 184184 a (Univ Nara Medical) Sep. 27, 2012.
Zeldich et al., The Neuroprotective Effect of Klotho is Mediated via Regulation of Members of the Redox System, Journal of Biological Chemistry, American Society for Biochemistry and Molecular Biology, vol. 289, No. 35, pp. 24700-24715, Jan. 1, 2014.
Extended European Search Report from Application No. 16747364. 4, dated Aug. 24, 2018.
Banks, W.A.; "Characteristics of compounds that cross the blood-brain barrier"; Drug Discovery for Neurodegeneration Conference; Proceedings of BMC Neurology; vol. 9 (Suppl I), S3; Jun. 12, 2009; 5 pages.
Chen, C.D. et al.; "Identification of Cleavage Sites Leading to the Shed Form of the Anti-Aging Protein Klotho"; Biochemistry; vol. 53; 2014; Aug. 11, 2014; pp. 5579-5587.
DiBona, D et al.; "Association of Klotho Polymorphisms with Healthy Aging: A Systematic Review and Meta-Analysis"; Rejuvenation Research; vol. 17, No. 2; 2014; pp. 212-217.
Lai, J.Y. et al.; "Open and shut: Crystal structures of the dodecylmaltoside solubilized mechanosensitive channel of small conductance from Escherichia coli and Helicobacter pylori at 4.4 A and 4.1 A resolutions"; Protein Science; vol. 22; 2013; pp. 502-509.
Leon, J. et al.; "Peripheral Elevation of a Klotho Fragment Enhances Brain Function and Resilience in Young, Aging, and alpha-Synuclein Transgenic Mice"; Cell Rep. Aug. 8, 2017; vol. 20, No. 6; pp. 1360-1371.
Masso A. et al.; "Secreted alpha-Klotho isoform protects against age-dependent memory deficits"; Molecular Psychiatry; 2017; 11 pages.
Matsumura, Y. et al.; "Identification of the Human Klotho Gene and Its Two Transcripts Encoding membrane and Secreted Klotho Protein"; Biochemical and Biophysical Research Communications; vol. 242; 1998; pp. 626-630.
Mucke, L., 1R01NS088532-01—Neurobiology and Therapeutic Potential of Klotho, grant abstract by the National Institutes of Health via the RePORT Expenditures and Results Tool (RePORTER) website; https://projectreporter.nih.gov/project_info_description.cfm?aid=8764612&icde=43822272; downloaded Mar. 21, 2019.
Xu, Y. et al.; "Molecular Basis of Klotho: From Gene to Function in Aging"; Endocrine Reviews; vol. 36, No. 2; Apr. 2015; pp. 174-193.
Office Action dated Sep. 29, 2019 from Chinese Application No. 201680019604.8 with cited references (not translated).
Chen Fei, et al., "Research Progress of the Association Between Senile Dementia and Klotho Gene," Journal of Modern Medicine & Health, vol. 30, No. 20, pp. 3077-3079, Oct. 30, 2014. (Original and translated documents.).
National Center for Biotechnology Information (NCBI) Reference Sequence NP_004786.2 as of Sep. 26, 2019.
Chen, et al., "Insulin stimulates the cleavage and release of the extracellular domain of Klotho by ADAM10 and ADAM17," PNAS, vol. 104 , No. 50, pp. 19796-19801, Dec. 11, 2007.
Zeldich, The Neuroprotective Effect of Klotho is Mediated via Regulation of Members of the Redox System, J. Biol. Chem., vol. 289, pp. 24700-24715 (2014).†
Dubal, Life Extension Factor Klotho Enhances Cognition, Cell Reports, vol. 7, pp. 1-12 (2014).†
Chen, The Antiaging Protein Klotho Enhances Oligodendrocyte Maturation and Myelination of the CNS, J. Neuroscience, vol. 33(5), pp. 1927-1939 (2013).†
Duce, Gene Profile Analysis Implicates Klotho as an Important Contributor to Aging Changes in Brain White Matter of the Rhesus Monkey, GLIA, vol. 56, pp. 106-117 (2008).†

\* cited by examiner
† cited by third party

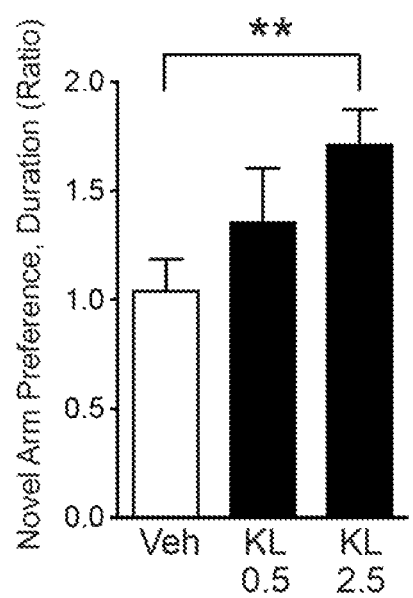
FIG. 3    Long Lasting Effect

SEQUENCE LISTING

<160> NUMBER OF SEQ ID NOS: 3

<210> SEQ ID NO 1
<211> LENGTH: 1012
<212> TYPE: PRT
<213> ORGANISM: Homo sapiens

<400> SEQUENCE: 1

Met Pro Ala Ser Ala Pro Pro Arg Arg Pro Pro Pro Pro Ser
1               5                   10                  15

Leu Ser Leu Leu Leu Val Leu Leu Gly Leu Gly Gly Arg Arg Leu Arg
                20                  25                  30

Ala Glu Pro Gly Asp Gly Ala Gln Thr Trp Ala Arg Phe Ser Arg Pro
            35                  40                  45

Pro Ala Pro Glu Ala Ala Gly Leu Phe Gln Gly Thr Phe Pro Asp Gly
        50                  55                  60

Phe Leu Trp Ala Val Gly Ser Ala Ala Tyr Gln Thr Glu Gly Gly Trp
65                  70                  75                  80

-continued

```
Gln Gln His Gly Lys Gly Ala Ser Ile Trp Asp Thr Phe Thr His His
            85                  90                  95

Pro Leu Ala Pro Pro Gly Asp Ser Arg Asn Ala Ser Leu Pro Leu Gly
        100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
    290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
    370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
        435                 440                 445

Gly Val Asp Val Ile Gly Tyr Thr Ala Trp Ser Leu Met Asp Gly Phe
    450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
```

```
            500                 505                 510
Gln Pro Leu Glu Gly Thr Phe Pro Cys Asp Phe Ala Trp Gly Val Val
            515                 520                 525

Asp Asn Tyr Ile Gln Val Asp Thr Thr Leu Ser Gln Phe Thr Asp Leu
            530                 535                 540

Asn Val Tyr Leu Trp Asp Val His His Ser Lys Arg Leu Ile Lys Val
545                 550                 555                 560

Asp Gly Val Val Thr Lys Lys Arg Lys Ser Tyr Cys Val Asp Phe Ala
                565                 570                 575

Ala Ile Gln Pro Gln Ile Ala Leu Leu Gln Glu Met His Val Thr His
            580                 585                 590

Phe Arg Phe Ser Leu Asp Trp Ala Leu Ile Leu Pro Leu Gly Asn Gln
            595                 600                 605

Ser Gln Val Asn His Thr Ile Leu Gln Tyr Tyr Arg Cys Met Ala Ser
            610                 615                 620

Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
                645                 650                 655

Trp Glu Asn Pro Tyr Thr Ala Leu Ala Phe Ala Glu Tyr Ala Arg Leu
                660                 665                 670

Cys Phe Gln Glu Leu Gly His His Val Lys Leu Trp Ile Thr Met Asn
            675                 680                 685

Glu Pro Tyr Thr Arg Asn Met Thr Tyr Ser Ala Gly His Asn Leu Leu
            690                 695                 700

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
                725                 730                 735

Pro Ala Cys Pro Phe Ser Gln Lys Asp Lys Glu Val Ala Glu Arg Val
                740                 745                 750

Leu Glu Phe Asp Ile Gly Trp Leu Ala Glu Pro Ile Phe Gly Ser Gly
            755                 760                 765

Asp Tyr Pro Trp Val Met Arg Asp Trp Leu Asn Gln Arg Asn Asn Phe
            770                 775                 780

Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
            805                 810                 815

Glu Lys Glu Asp Pro Ile Lys Tyr Asn Asp Tyr Leu Glu Val Gln Glu
            820                 825                 830

Met Thr Asp Ile Thr Trp Leu Asn Ser Pro Ser Gln Val Ala Val Val
            835                 840                 845

Pro Trp Gly Leu Arg Lys Val Leu Asn Trp Leu Lys Phe Lys Tyr Gly
            850                 855                 860

Asp Leu Pro Met Tyr Ile Ile Ser Asn Gly Ile Asp Asp Gly Leu His
865                 870                 875                 880

Ala Glu Asp Asp Gln Leu Arg Val Tyr Tyr Met Gln Asn Tyr Ile Asn
                885                 890                 895

Glu Ala Leu Lys Ala His Ile Leu Asp Gly Ile Asn Leu Cys Gly Tyr
            900                 905                 910

Phe Ala Tyr Ser Phe Asn Asp Arg Thr Ala Pro Arg Phe Gly Leu Tyr
            915                 920                 925
```

```
Arg Tyr Ala Ala Asp Gln Phe Glu Pro Lys Ala Ser Met Lys His Tyr
    930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
                965                 970                 975

His Thr Arg Lys Ser Leu Leu Ala Phe Ile Ala Phe Leu Phe Phe Ala
            980                 985                 990

Ser Ile Ile Ser Leu Ser Leu Ile Phe Tyr Tyr Ser Lys Lys Gly Arg
        995                 1000                1005

Arg Ser  Tyr Lys
    1010

<210> SEQ ID NO 2
<211> LENGTH: 15
<212> TYPE: PRT
<213> ORGANISM: Homo sapiens

<400> SEQUENCE: 2

Asp Thr Thr Leu Ser Gln Phe Thr Asp Leu Asn Val Tyr Leu Trp
1               5                   10                  15

<210> SEQ ID NO 3
<211> LENGTH: 15
<212> TYPE: PRT
<213> ORGANISM: Homo sapiens

<400> SEQUENCE: 3

Ser Gln Leu Thr Lys Pro Ile Ser Ser Leu Thr Lys Pro Tyr His
1               5                   10                  15
```

METHODS AND COMPOSITIONS FOR IMPROVED COGNITION

CROSS-REFERENCE TO RELATED PATENT APPLICATIONS

The present application is a U.S. National Phase Application of PCT/US2016/016842, filed Feb. 5, 2016 which claims benefit of priority to U.S. Provisional Patent Application No. 62/113,300, filed Feb. 6, 2015, each of which are incorporated by reference.

STATEMENT AS TO RIGHTS TO INVENTIONS MADE UNDER FEDERALLY SPONSORED RESEARCH AND DEVELOPMENT

This invention was made with government support under grant no. K08 AG034531 awarded by the National Institutes of Health. The government has certain rights in the invention.

REFERENCE TO SUBMISSION OF A SEQUENCE LISTING AS A TEXT FILE

The Sequence Listing written in file SEQ_LISTING_1055233.txt created on Jul. 25, 2017, 9,417 KB, machine format IBM-PC, MS-Windows operating system, is hereby incorporated by reference in its entirety for all purposes.

BACKGROUND OF THE INVENTION

Brain health is one of the biggest biomedical challenges with few if any effective medical treatments. Cognition is a highly valued and central manifestation of brain health that is impaired or becomes disrupted in normal aging, numerous neurodegenerative, neurologic, and psychiatric diseases, childhood developmental syndromes, traumatic brain injury, and stress. Cognition is also disrupted by jet lag, medication side effects, and certain medical treatments, such as those for cancer. Thus, the potential to enhance cognition or counter cognitive dysfunction is of enormous relevance across the human lifespan in health and disease.

BRIEF SUMMARY OF THE INVENTION

Provided herein are methods and compositions for improving cognition through systemic administration of klotho or a protein comprising klotho or a functional fragment thereof. In some embodiments, the method comprises improving cognition in an individual comprising administering to the individual an effective amount of a protein comprising a Klotho polypeptide or a functional variant or fragment thereof, thereby improving cognitive function in the individual. In some embodiments, the administering is systemic, peripheral, or nasal. In some embodiments, the protein is the Klotho polypeptide or a fragment thereof. In some embodiments, the administering is oral, mucosal, or carried out by injection. In some embodiments, the injection is intravenous, intraperitoneal, subcutaneous, or intramuscular. In some embodiments, the administration is by infusion, e.g., continuous infusion using a reservoir or osmotic minipump.

In some embodiments, the individual is a human. In some embodiments, the human has at least normal cognitive function and the administering results in improved cognitive function compared to before the administering. In some embodiments, the human is 50 years of age or older (e.g., at least 60, 65, 70, 75, 80, 85, 90, 100, or older). In some embodiments, the individual is experiencing age-related cognitive decline. In some embodiments, the administering results in a reduced rate of cognitive decline, e.g., so that short term memory does not decline as quickly as expected based on pre-treatment or age-cohort decline. In some embodiments, the individual is less than 50 years of age.

In some embodiments, the individual has a neurodegenerative disease, e.g., Alzheimer's disease, Parkinson's disease, Huntington's disease, frontotemporal dementia, progressive supranuclear palsy, corticobasalar degeneration, mild cognitive impairment, vascular dementia, Lewy body dementia, multiple system atrophy, amyotropic lateral sclerosis, prion disorder, and HIV-related dementia. In some embodiments, the individual has a mental or mood disorder, e.g., depression, schizophrenia, attention deficit/hyperactivity disorder, autism spectrum disorder, intellectual disability, a mood disorder, or a psychotic disorder. In some embodiments, the individual has a condition selected from traumatic brain injury, stroke, multiple sclerosis, neuroautoimmune disease, epilepsy, delirium, and a paraneoplastic disorder. In some embodiments, the individual has a condition selected from X-linked mental disorder, Down's syndrome, Angelman's syndrome, and Rett's syndrome. In some embodiments, the individual has a condition selected from phenylketonuria, Lesch-Nyhan, galactosemia, and adrenoleukodystrophy. In some embodiments, the individual is receiving radiation treatment or chemotherapy for cancer. In some embodiments, the individual is experiencing or is expected to experience (e.g., in about 2 hours to 2 weeks, about 12-48 hours, or about 24 hours) stress, pain, sleep deprivation, or jet lag.

In some embodiments, the human has impaired motor function the administering results in improved motor function compared to before the administering.

In some embodiments, the klotho polypeptide has at least 75% identity (e.g., at least 80, 85, 90, 91, 92, 93, 94, 95, 96, 97, 98, 99, or 100% identity) to soluble human klotho (amino acids 34-979 of SEQ ID NO:1). In some embodiments, the klotho polypeptide is a functional fragment comprising a polypeptide with at least 75% identity (e.g., at least 80, 85, 90, 91, 92, 93, 94, 95, 96, 97, 98, 99, or 100% identity) to the KL1 domain of human klotho. In some embodiments, the klotho polypeptide is a functional fragment comprising a polypeptide with at least 75% identity (e.g., at least 80, 85, 90, 91, 92, 93, 94, 95, 96, 97, 98, 99, or 100% identity) to the KL2 domain of human klotho. In some embodiments, the klotho polypeptide retains at least 40, 50, 60, 70, 80, 90, or 100% of the level of at least one activity of soluble human klotho.

In some embodiments, the klotho polypeptide is administered to the individual at a dose of 0.1-50,000 µg/kg body weight (e.g., 0.5-10 µg/kg, 0.5-500 µg/kg, 1-2000 µg/kg, 1-250 µg/kg, 5-250 µg/kg, 10-100 µg/kg, 1000-20,000 µg/kg, or about 10, 25, 50, 100, or 1000 µg/kg). In some embodiments, the klotho polypeptide is administered daily, twice per week, weekly, or every two weeks. In some embodiments, the klotho polypeptide is administered prior to (e.g., 2, 6, 12, 24, or 48 hours) or in response to an event requiring heightened cognition, e.g., stress, jet lag, sleep deprivation, or anticipated taxing mental task.

In some embodiments, the individual is tested for cognitive ability prior to the administering. In some embodiments, the individual is tested for cognitive ability after the administering. In some embodiments, the individual is tested for cognitive ability before and after the administering, or multiple times during the course of treatment. In some embodiments, the individual is tested for semantic, episodic, procedural, priming, and/or working memory. In some embodiments, the individual is tested for language ability, executive function, visuospatial function, or dementia. In some embodiments, the dose or frequency of administration of klotho polypeptide is increased when cognitive ability does not significantly increase.

In some embodiments, a method of improving motor function is provided. In some embodiments, a method is provided for improving motor function in an individual in need thereof, the method comprising administering to the individual an effective amount of a protein comprising a Klotho polypeptide or a functional fragment thereof, wherein the administering is systemic or peripheral, thereby improving motor function in the individual compared to before the administering. In some embodiments, the klotho polypeptide has at least 75% identity (e.g., at least 80, 85, 90, 91, 92, 93, 94, 95, 96, 97, 98, 99, or 100% identity) to soluble human klotho (amino acids 34-979 of SEQ ID NO:1). In some embodiments, the klotho polypeptide is a functional fragment comprising a polypeptide with at least 75% identity (e.g., at least 80, 85, 90, 91, 92, 93, 94, 95, 96, 97, 98, 99, or 100% identity) to the KL1 domain of human klotho. In some embodiments, the klotho polypeptide is a functional fragment comprising a polypeptide with at least 75% identity (e.g., at least 80, 85, 90, 91, 92, 93, 94, 95, 96, 97, 98, 99, or 100% identity) to the KL2 domain of human klotho. In some embodiments, the klotho polypeptide retains at least 40, 50, 60, 70, 80, 90, or 100% of the level of at least one activity of soluble human klotho. In some embodiments, the klotho polypeptide is administered to the individual at a dose of 0.1-50,000 µg/kg body weight (e.g., 0.5-10 µg/kg, 0.5-500 µg/kg, 1-2000 µg/kg, 1-250 µg/kg, 5-250 µg/kg, 10-100 µg/kg, 1000-20,000 µg/kg, or about 10, 25, 50, 100, or 1000 µg/kg). In some embodiments, the klotho polypeptide is administered daily, twice per week, weekly, or every two weeks.

In some embodiments, the individual with impaired motor function has stroke to the brain or spinal cord (ischemic or hemorrhagic), neurodegenerative disease (Parkinson's disease, Lewy body dementia, multiple system atrophy, amyotropic lateral sclerosis, prion disorder, Huntington's disease, supranuclear palsy), Parkinsonism, traumatic brain injury, neuroinfectious brain lesions, multiple sclerosis and related autoimmune and demyelinating disease, spinal cord lesions (compressive, infectious, toxic or metabolic, autoimmune, oncologic), brain tumor, epilepsy, paraneoplastic disorder, neurodevelopmental disorder (mitochondrial, autosomal genetic), muscle disease (polymyositis, dermatomyositis, inclusion body myositis, infectious, endocrine, metabolic, toxic, congenital myopathy, congenital muscular dystrophy, hereditary), neuropathies (Guillain-Barre syndrome, axonal and demyelinating, diabetic, toxic, metabolic, infectious, critical illness, entrapment), tick paralysis, myasthenia gravis, and spinal muscular atrophy.

BRIEF DESCRIPTION OF THE DRAWINGS

FIG. 1A. Mice were tested in the Y maze 18 hrs after treatment with vehicle or klotho. Percent alternations among arms during 4 minutes of exploration of a Y maze are shown (n=4 male mice/group).

FIG. 1B-J. Mice were tested in the Morris water maze after daily treatment with vehicle or klotho (two independent cohorts shown: Cohort 1 and Cohort 2).

FIG. 1B. Spatial learning curves when the platform is hidden are shown in Cohort 1. Veh or KL was administered 4 h prior to testing. Data represent the daily average of total distance traveled on Days 1-4 to reach the hidden platform. Day 0 represents distance traveled on the first trial of Day 1. On Day 5, when the platform was visible, Veh- and klotho-treated mice located it equally well. (n=4 male mice/group)

FIG. 1C. Veh- and klotho-treated mice swam at equal speeds in Cohort 1, as measured by the average velocity from hidden training on Day 4.

FIG. 1D. Spatial learning curves when the platform is hidden are shown in an independent cohort of mice, Cohort 2. Veh or KL was administered 18 h prior to testing. Data represent the daily average of distance traveled on Days 1-4 to reach the hidden platform. (n=7-10 mice/group; males and females included)

FIG. 1E-J. Results of probe trials to assess spatial memory when the platform was removed 1 hr and 24 hrs after completion of hidden-platform training in Veh- and klotho-treated mice in Cohort 1.

FIG. 1E. Duration at the target center in a 1 hr probe shows time spent at the original platform location.

FIG. 1F. Target platform crossings in a 1 hr probe shows the frequency of crossings over the original platform location.

FIG. 1G. Percent time spent in the target quadrant, compared to the average time spent in other quadrants, in a 1 hr probe. *$p<0.05$ (t-test)

FIG. 1H. Duration at the target center in a 24 hr probe.

FIG. 1I. Target platform crossings in a 24 hr probe.

FIG. 1J. Percent time spent in the target quadrant in a 24 hr probe.

(FIG. 2A) Novel arm preference is shown as a ratio time spent in the novel compared to the familiar arm throughout indicated times of exploration and (FIG. 2B) at 3 minutes. *$p<0.05$ (t-test). Data are mean±SEM.

FIG. 3. Acute delivery of klotho induces long-lasting cognitive enhancement. Mice were tested for spatial and working memory in the large Y-Maze at 16 days following the last i.p. delivery of vehicle (Veh) or recombinant mouse klotho (KL) (0.5 or 2.5 µg/kg) that was given daily for 5 days (n=8-10 mice per experimental group, sex-balanced groups, age 5-5.5 months of age). Duration of time spent in the novel arm and the familiar arm was measured during exploration of the maze 18 hours after training. Novel arm preference is shown as a ratio of time spent in the novel compared to the familiar arm at 5 min of exploration. **$p=0.01$ (Bonferroni-Holm test). Data are mean±SEM.

Duration of time and number of entries in the novel and familiar arms were measured during exploration of the maze 18 hours after training. Data are mean±SEM.

Figure 4A:
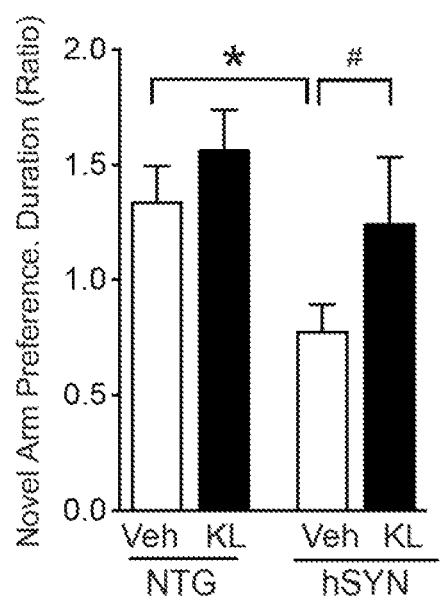
FIG. 4A-B. Acute delivery of klotho improves cognitive deficits in transgenic hSYN mice that express the human α-synuclein protein. Mice were tested for spatial and working memory in the large Y-Maze following i.p. delivery of vehicle (Veh) or recombinant mouse klotho (KL) (2.5 µg/kg) at 22 hours prior to training and then 14 hours prior to testing (n=6-9 male mice per group, age 2.5-6 months of age).

FIG. 4A. Novel arm preference is shown as ratio of time spent in the novel compared to the familiar arm at 5 min of exploration. Two-way ANOVA: hSYN effect p=0.026, KL effect p=0.07; *p<0.05, # p=0.07 (Bonferroni-Holm test)

Figure 4B:
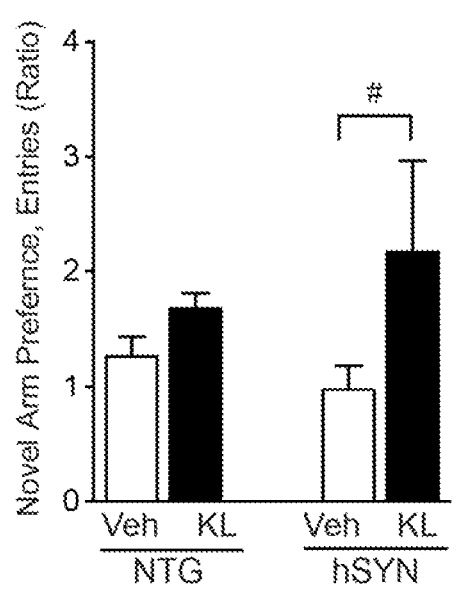

FIG. 4B. Novel arm preference is shown as ratio of entries into the novel compared to the familiar arm at 5 min of exploration. Two-way ANOVA: hSYN effect p=0.07, KL effect p=0.03; # p=0.07 (t-test).

Figure 5:
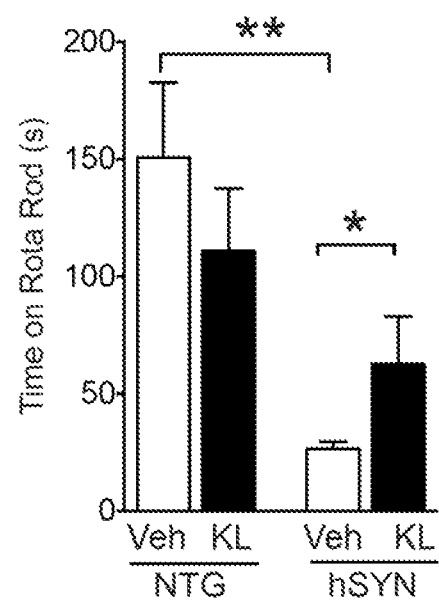

FIG. 5. Acute delivery of klotho improves early motor deficits in transgenic hSYN mice that express the human α-synuclein protein. Mice were tested for motor function on the rotarod task following i.p. delivery of vehicle (Veh) or recombinant mouse klotho (KL) (2.5 µg/kg) at approximately 17 hours prior to testing (n=6-10 male mice per experimental group, age 2.5-6 months of age). Time spent on the spinning rod without falling is depicted in seconds (s). In hSYN mice, KL-treatment improves early motor function as shown by increased duration of the average time spent on the spinning rod during Trials 1 through 3. Two-way ANOVA: hSYN effect 0.0025; **p<0.01, *p<0.05 (Bonferroni-Holm test). Data are mean±SEM.

Figure 6:
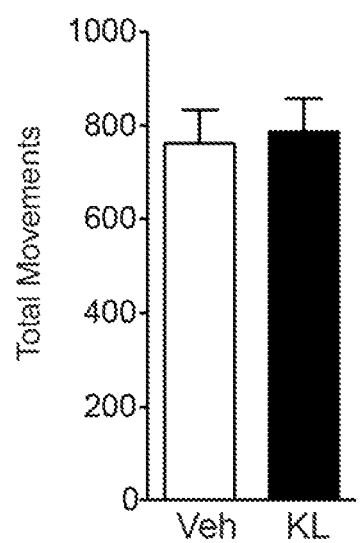

FIG. 6. Acute delivery of klotho does not alter the overall activity of mice. Mice were tested for level of overall movements and total activity in the open field task at 16 hours following i.p. delivery of vehicle (Veh) or recombinant mouse klotho (KL) (2.5 µg/kg) (n=8 mice per experimental group; sex-balanced groups; age 5 months). Total movements over 5 minutes are depicted. Data are mean±SEM.

DETAILED DESCRIPTION OF THE INVENTION

I. Introduction

Klotho is a relatively large protein, approximately 130 kD in its secreted form, and is not expected to cross the blood-brain barrier. The results provided herein, however, show that Klotho exerts a positive effect on cognition within hours of systemic administration and long after its half-life elimination. These results are highly unexpected, and provide the advantage of safer, more convenient therapies compared to administration directly to the brain or into the cerebrospinal fluid.

II. Definitions

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4th ed. 2007); Sambrook et al., MOLECULAR CLONING, A LABORATORY MANUAL, Cold Springs Harbor Press (Cold Springs Harbor, N.Y. 1989). Any methods, devices and materials similar or equivalent to those described herein can be used in the practice of this invention. The following definitions are provided to facilitate understanding of certain terms used frequently herein and are not meant to limit the scope of the present disclosure.

The terms "klotho" or "klotho polypeptide" refer to soluble klotho polypeptide, and functional variants and fragments thereof, unless otherwise stated. Soluble klotho is any form of klotho that circulates in fluid (e.g., serum, cerebrospinal fluid, etc.), and that does not include a transmembrane or intracellular component. Klotho can be cleaved from its transmembrane form and released into fluid, or otherwise secreted or shed from a cell. Klotho RNA can also be alternatively spliced and directly secreted into the surrounding fluid (i.e., without forming a transmembrane protein). Both forms are encompassed in the terms soluble klotho polypeptide, klotho polypeptide, and klotho.

As used herein, the terms "systemic" or "peripheral" refer to administration by a route that does not involve direct injection (or other administration) into the cerebrospinal fluid (CSF) or central nervous system (CNS). That is, systemic and peripheral administration encompasses administration to the "blood" side of the blood-brain barrier. Examples of systemic and peripheral routes include oral and mucosal, intravenous, intraperitoneal, intramuscular, and subcutaneous injection, and intravenous drip.

The terms "cognition," "cognitive ability," "cognitive function," and like terms refer to a collection of mental tasks and functions, including but not limited to: memory (e.g., semantic, episodic, procedural, priming, or working); orientation; language; problem solving; visual perception, construction, and integration; planning; organizational skills; selective attention; inhibitory control; and ability to mentally manipulate information.

The terms "improved cognition," "increased cognitive ability," "improved cognitive function," and like terms refer to an improvement in cognition under a given condition (e.g. treatment with klotho) compared to cognition absent the condition (e.g., absent treatment with klotho). For an individual experiencing cognitive decline, an improvement in cognition might be a reduction in the rate of cognitive decline (i.e., an improvement compared to the absence of treatment), but not an actual improvement in cognitive ability. An increase in cognitive ability can also be an increase in brain activity in a specified area, e.g., as determined by MRI, or an inhibition of brain activity that results in better overall brain function. An increase in cognitive ability can also be improvement in a cognitive performance test as described in more detail herein. An improvement or increase in cognitive ability can be in any one cognitive aspect or function, or any combination of individual cognitive functions.

An individual in need of improved cognitive function refers to individuals with age-related cognitive decline; a neurodegenerative disease; a mental or mood disorder; traumatic brain injury; developmental delay; genetic disorder resulting in reduced cognitive ability; brain injury due to stroke, brain cancer, MS, epilepsy, radiation or chemotherapy; etc. An individual in need of improved cognitive function can also include individuals that desire increased mental function to fight the effects of stress, sleep deprivation, jet lag, or pain, or to heighten ability for a particular task. A more complete and specific list of such individuals in included in the "Cognitive conditions and disorders" section herein.

The words "protein", "peptide", and "polypeptide" are used interchangeably to denote an amino acid polymer or a set of two or more interacting or bound amino acid polymers. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, often silent variations of a nucleic acid which encodes a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following amino acids are typically conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

The terms "identical" or "percent identity," in the context of two or more nucleic acids, or two or more polypeptides, refer to two or more sequences or subsequences that are the same or have a specified percentage of nucleotides, or amino acids, that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters, or by manual alignment and visual inspection. See e.g., the NCBI web site at ncbi.nlm.nih.gov/BLAST. Such sequences are then said to be "substantially identical." This definition also refers to, or may be applied to, the compliment of a nucleotide test sequence. The definition also includes sequences that have deletions and/or additions, as well as those that have substitutions. As described below, the algorithms can account for gaps and the like. Typically, identity exists over a region comprising an antibody epitope, or a sequence that is at least about 25 amino acids or nucleotides in length, or over a region that is 50-100 amino acids or nucleotides in length, or over the entire length of the reference sequence.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a protein or nucleic acid indicates that the protein or nucleic acid comprises two or more subsequences that are not found in the same relationship to each other in nature. For instance, the protein or nucleic acid is typically recombinantly produced, having two or more sequences from unrelated genes arranged to make a new functional nucleic acid, e.g., a promoter from one source and a coding region from another source, or functional chimeric protein.

The terms "agonist," "activator," "inducer" and like terms refer to an agent that increases activity or expression (e.g., of klotho or a klotho signaling pathway) as compared to a control. Agonists are agents that, e.g., stimulate, increase, activate, enhance activation, sensitize or upregulate the activity of klotho or a klotho signaling pathway. The expression or activity can be increased 10%, 20%, 30%, 40%, 50%, 60%, 70%, 80%, 90% 100% or more than that in a control. In certain instances, the activation is 1.5-fold, 2-fold, 3-fold, 4-fold, 5-fold, 10-fold, or more in comparison to a control.

The terms "inhibitor," "repressor" or "antagonist" or "downregulator" interchangeably refer to a substance that results in a detectably lower expression or activity level as compared to a control. The inhibited expression or activity can be 10%, 20%, 30%, 40%, 50%, 60%, 70%, 80%, 90% or less than that in a control. In certain instances, the inhibition is 1.5-fold, 2-fold, 3-fold, 4-fold, 5-fold, 10-fold, or more in comparison to a control.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of benefit and/or side effects). Controls can be designed for in vitro applications. One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

A "label" or a "detectable moiety" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any method known for conjugating a protein to the label may be employed, e.g., using methods described in Hermanson, *Bioconjugate Techniques* 1996, Academic Press, Inc., San Diego.

A "labeled" molecule (e.g., klotho polypeptide) is one that is bound, either covalently, through a linker or a chemical bond, or noncovalently, through ionic, van der Waals, electrostatic, or hydrogen bonds to a label such that the presence of the molecule may be detected by detecting the presence of the label bound to the molecule.

The term "diagnosis" refers to a relative probability that a disorder is present in an individual. Similarly, the term "prognosis" refers to a relative probability that a certain future outcome may occur in the individual. For example, in the context of the present disclosure, prognosis can refer to the likelihood that an individual suffer cognitive decline, or the likely severity of the disease (e.g., severity of symptoms, rate of functional decline, etc.). The terms are not intended to be absolute, as will be appreciated by any one of skill in the field of medical diagnostics.

A "biological sample" can be obtained from a patient, e.g., a biopsy, from an animal, such as an animal model, or from cultured cells, e.g., a cell line or cells removed from a patient and grown in culture for observation. Biological samples include tissues and bodily fluids, e.g., cerebrospinal fluid (CSF), blood, blood fractions, lymph, saliva, urine, feces, etc.

The terms "therapy," "treatment," and "amelioration" refer to any reduction in the severity of symptoms (cognitive decline), or improvement in cognitive function, or where motor function is affected, an improvement in motor function. As used herein, the terms "treat" and "prevent" are not intended to be absolute terms. Treatment and prevention can refer to any delay in cognitive decline, amelioration of symptoms (e.g., confusion, delirium), etc. Treatment and prevention can be complete or partial, such that cognition is better than would be expected without treatment (e.g., compared to cognition in the same individual before treatment or compared to cognition in similar non-treated individuals). The effect of treatment can be compared to an individual or pool of individuals not receiving the treatment, or to the same patient prior to treatment or at a different time during treatment. In some aspects, cognition is improved by at least 1%, as compared, e.g., to the individual before administration or to a control individual not undergoing treatment. In some embodiments, cognition is improved by at least 2, 3, 5, 7, 10, 15, 20, 25%, 50%, 75%, 80%, or 90%, or more, determined using tests of cognition, molecular proxies, or structural changes associated with brain function. In some aspects, motor function is improved by at least 1%, as compared, e.g., to the individual before administration or to a control individual not undergoing treatment. In some embodiments, motor function is improved by at least 2, 3, 5, 7, 10, 15, 20, 25%, 50%, 75%, 80%, or 90%, or more, determined using tests of motor function.

The terms "effective amount," "effective dose," "therapeutically effective amount," etc. refer to that amount of the therapeutic agent sufficient to ameliorate a disorder, as described above. For example, for the given parameter, a therapeutically effective amount will show an increase or decrease of therapeutic effect at least 1%, 2%, 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

As used herein, the term "pharmaceutically acceptable" is used synonymously with physiologically acceptable and pharmacologically acceptable. A pharmaceutical composition will generally comprise agents for buffering and preservation in storage, and can include buffers and carriers for appropriate delivery, depending on the route of administration.

The terms "dose" and "dosage" are used interchangeably herein. A dose refers to the amount of active ingredient given to an individual at each administration. For the present invention, the dose refers to the amount of Klotho polypeptide. The dose will vary depending on a number of factors, including frequency of administration; size and tolerance of the individual; type and severity of the condition; risk of side effects; and the route of administration. One of skill in the art will recognize that the dose can be modified depending on the above factors or based on therapeutic progress. The term "dosage form" refers to the particular format of the pharmaceutical, and depends on the route of administration. For example, a dosage form can be in a liquid, e.g., a saline solution for injection.

"Subject," "patient," "individual" and like terms are used interchangeably and refer to, except where indicated, mammals such as humans and non-human primates, as well as dogs, horses, pigs, mice, rats, and other mammalian species. The term does not necessarily indicate that the subject has been diagnosed with a particular disease, but typically refers to an individual under medical supervision. A patient can be an individual that is seeking treatment, monitoring, adjustment or modification of an existing therapeutic regimen, etc.

III. Klotho

Klotho is a pleiotropic protein and an aging regulator that circulates throughout the body and brain (Imura et al. (2004) *FEBS Letters* 565:143; Kurosu et al. (2005) *Science* 309: 1829). Human Klotho is described in GenBank Accession No. NC_000013 and Uniprot Accession No. Q9UEF7. A number of species homologs exist, including mouse and rat Klotho which share 86% and 85% identity with the human Klotho polypeptide, which is shown as SEQ ID NO:1. It exists in a transmembrane form that can be cleaved such that the extracellular portion (amino acids 34-979) is released as a hormone (Shiraki-lika et al. (1998) *FEBS Letters* 424:6).

Klotho also has a splice variant that results in a 549 amino acid secreted form of the protein that is also functional (Wang and Sun (2009) *Ageing Res. Rev.* 8:43). Both cleaved and secreted klotho are soluble and functional in the body, but have a sequence variation at the C-terminal end due to the splice variation. Amino acids 535-549 are DTTLSQFT-DLNVYLW (SEQ ID NO:2) for cleaved, soluble human Klotho and SQLTKPISSLTKPYH (SEQ ID NO:3) for spliced, soluble human Klotho. Full length soluble Klotho includes two conserved domains (KL1 and KL2) with homology to beta glycosidase proteins. The conserved beta-glucosidase/6-phospho-beta-glucosidase/beta-galactosidase motif spans 62-497 in the human protein and 64-499 in the mouse. The conserved KL1 sequence is described in Chateau et al. (2010) *Aging* 2:567 and Matsumura et al. (1998) *Biochem Biophys Res Commun*, and comprises amino acids 34-549 of the human Klotho protein, with the glycosyl hydrolase consensus region spanning amino acids 57-506 of the human Klotho protein (59-508 of the mouse). Klotho does not have beta-glycosidase activity, but shows some beta-glucuronidase activity.

Klotho suppresses insulin and wnt signaling, regulates ion channels and their transport, and promotes function of FGF23. See, e.g., Chang et al. (2005) *Science* 310:490; Imura et al. (2007) *Science* 316:1615; Kurosu (2005); Liu et al. (2007) *Science* 317:803; and Urakawa et al. (2006) *Nature* 444:770).

In mice, transgenic overexpression of klotho extends lifespan and associates with better cognitive functions in the normal and diseased brain (Kurosu (2005); Dubal et al. (2014) *Cell Reports* 7:1065; Dubal et al. (2015) *J. Neuroscience*). In humans, a single allele of the KL-VS variant of the KLOTHO gene, which increases secreted klotho promotes longevity (Arking et al., 2002; Arking et al., 2005; Invidia et al., 2010) and also associates with better baseline cognitive functions in aging populations. See, e.g., Arking et al. (2002) *PNAS* 99:856; Arking et al. (2005) *Circ. Res.* 96:412; Dubal et al (2014) *Cell Reports* 7:1065; Yokoyama et al. (2015) *Ann. Clin. Translational Neurology* 2:215.

Klotho polypeptides that can be used for administration include species homologs (e.g., non-human primate, mouse, rat), allelic variants, functional fragments, and functional variants of the wild type sequence that retain cognition improving activity. Examples include secreted Klotho, fragments comprising the KL1 domain, fragments comprising the KL2 domain, fragments comprising the KL1 and KL2 domains, variants comprising the KL1 domain with at least one (e.g., 1-20, 5-50, 25-100) non-conserved amino acid in the KL1 domain substituted with a different amino acid or deleted, variants comprising the KL2 domain with at least one non-conserved amino acid in the KL2 domain substituted with a different amino acid.

Functional fragments of the Klotho polypeptide that can be used as described herein include the extracellular domain (e.g., corresponding to or substantially identical or similar to amino acids 34-979 of human Klotho), secreted Klotho (e.g., corresponding to or substantially identical or similar to 549 amino acid form), a KL1 domain (e.g., corresponding to or substantially identical or similar to amino acids 34-549 of human Klotho), a glycosyl hydrolase consensus sequence (e.g., corresponding to or substantially identical or similar to amino acids 57-506 of human Klotho), or a beta-glucosidase/6-phospho-beta-glucosidase/beta-galactosidase consensus sequence (e.g., corresponding to or substantially identical or similar to amino acids 62-497 of human Klotho). In some embodiments, the Klotho polypeptide comprises or is substantially identical or similar to amino acids 34-549 of human Klotho. In some embodiments, the Klotho polypeptide is part of a larger fusion protein. In some embodiments, the fusion protein comprises the Klotho polypeptide as described herein and further comprises no more than 100, 75, 50, or 30 additional amino acids. In some embodiments, the Klotho polypeptide is not fused to a Fibroblast growth factor (FGF). In some embodiments, the Klotho polypeptide comprises (e.g., is fused to) an affinity tag (e.g., a histidine tag) or a conjugate to increase stability or half-life in vivo.

A functional variant or fragment of Klotho is a variant or fragment that retains any klotho activity, e.g., at least 20%, 30%, 40%, 50%, 60%, 70%, 80%, 90%, or 100% of the level of any activity of soluble klotho. Soluble klotho activities include those described above, and include binding FGF-23, binding to FGFR1c, beta-glucuronidase activity, suppression of wnt signaling, suppression of insulin signaling, suppression of TFG-beta 1 activity, increasing GluN2B expression and/or synaptic localization, c-fos induction. Additional Klotho activities include causing changes in magnetic resonance imaging (MRI) brain scans, e.g., functional MM, electroencephalograph (EEG), and transcranial magnetic and electrical stimulation (TMS and TES); and improved performance in neuropsychologic testing and cognitive ability.

IV. Administration of Klotho

Provided herein are methods of improving cognition and/or motor function in an individual comprising administering Klotho to the individual. In some embodiments, the method of treatment comprises administering to an individual an effective amount of a Klotho polypeptide (or functional variant or fragment thereof). In some embodiments, the treatment is prophylactic, e.g., for individual expecting stress (e.g., jet lag, military performance) or to prevent cognitive decline associated with aging. In some embodiments, the individual has been diagnosed with a cognitive disorder. In some embodiments, the individual is receiving or has received therapy for a cognitive disorder or for a condition that is related to cognitive function (e.g., cognitive decline in response to chemotherapy).

In some embodiments, the method further comprises monitoring the individual for cognitive ability, either through a molecular proxy (e.g., changes NMDA receptor or c-fos activation, or GluN2B levels in the brain), changes in MRI brain scans (e.g., functional MRI), changes in EEG, changes in TMS and TES, changes in neuropsychologic test scores, or tests of cognitive ability (e.g., for learning, short or long term memory, executive functions, language ability, and visuospatial function). In some embodiments, the individual is monitored using more than one of the above tests in any combination. In some embodiments, the dose of the Klotho polypeptide for each administration is determined based on the therapeutic progress of the individual, e.g., where a higher dose is administered if the individual is not responding sufficiently to therapy.

In some embodiments, the Klotho polypeptide is administered in a pharmaceutical composition with a physiologically (i.e., pharmaceutically) acceptable carrier. The term "carrier" refers to a typically inert substance used as a diluent or vehicle for a diagnostic or therapeutic agent. The term also encompasses a typically inert substance that imparts cohesive qualities to the composition. Physiologically acceptable carriers can be liquid, e.g., physiological saline, phosphate buffer, normal buffered saline (135-150 mM NaCl), water, buffered water, 0.4% saline, 0.3% glycine, glycoproteins to provide enhanced stability (e.g., albumin, lipoprotein, globulin, etc.), and the like. Since physiologically acceptable carriers are determined in part by the particular composition being administered as well as by the particular method used to administer the composition, there are a wide variety of suitable formulations of pharmaceutical compositions of the present invention (See, e.g., Remington's Pharmaceutical Sciences, 17$^{th}$ ed., 1989).

The presently described compositions can be sterilized by conventional, well-known sterilization techniques or may be produced under sterile conditions. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents, wetting agents, and the like, e.g., sodium acetate, sodium lactate, sodium chloride, potassium chloride, calcium chloride, sorbitan monolaurate, and triethanolamine oleate. Sugars can also be included for stabilizing the compositions, such as a stabilizer for lyophilized antibody compositions.

Dosage forms can be prepared for mucosal (e.g., nasal, sublingual, vaginal, buccal, or rectal), parenteral (e.g., subcutaneous, intravenous, intramuscular, or intraarterial injection, either bolus or infusion), oral, or transdermal administration to a patient. Examples of dosage forms include, but are not limited to: dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

Injectable compositions can comprise a solution of the Klotho polypeptide suspended in an acceptable carrier, such as an aqueous carrier. Any of a variety of aqueous carriers can be used, e.g., water, buffered water, 0.4% saline, 0.9% isotonic saline, 0.3% glycine, 5% dextrose, and the like, and may include glycoproteins for enhanced stability, such as albumin, lipoprotein, globulin, etc. In some embodiments, normal buffered saline (135-150 mM NaCl) is used. The compositions can contain pharmaceutically acceptable auxiliary substances to approximate physiological conditions, such as pH adjusting and buffering agents, tonicity adjusting agents, wetting agents, e.g., sodium acetate, sodium lactate, sodium chloride, potassium chloride, calcium chloride, sorbitan monolaurate, triethanolamine oleate, etc.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Injection solutions and suspensions can also be prepared from sterile powders, granules, and tablets. In some embodiments, the composition is administered by intravenous infusion, topically, intraperitoneally, intravesically, or intrathecally. The Klotho polypeptide formulation can be provided in unit-dose or multi-dose sealed containers, such as ampoules and vials.

The Klotho polypeptide composition, alone or in combination with other suitable components, can be made into aerosol formulations ("nebulized") to be administered via inhalation. Aerosol formulations can be placed into pressurized acceptable propellants, such as dichlorodifluoromethane, propane, and nitrogen.

The pharmaceutical preparation can be packaged or prepared in unit dosage form. In such form, the preparation is subdivided into unit doses containing appropriate quantities of the active component, e.g., according to the dose of Klotho polypeptide. The unit dosage form can be a packaged preparation, the package containing discrete quantities of preparation. The composition can, if desired, also contain other compatible therapeutic agents. In some embodiments, the Klotho polypeptide composition can be formulated in a kit for administration.

In some embodiments, a pharmaceutical composition comprising a klotho polypeptide is administered orally. In some embodiments, a pharmaceutical composition comprising a klotho polypeptide is administered mucosally, e.g., nasally. In some embodiments, a pharmaceutical composition comprising a klotho polypeptide is administered by injection, e.g., subcutaneous, intraperitoneal, intravenous, or intramuscular. In some embodiments, a pharmaceutical composition comprising a klotho polypeptide is administered by infusion, e.g., using a reservoir or osmotic minipump.

An example of administration of a pharmaceutical composition includes storing the Klotho polypeptide at 10 mg/ml in sterile isotonic aqueous saline solution at 4° C., and diluting it in an appropriate solution for injection prior to administration to the patient. In some embodiments, the Klotho polypeptide composition can be administered by intravenous infusion over the course of 0.25-2 hours. In some embodiments, the administration procedure is via bolus injection.

In therapeutic use, the Klotho polypeptide can be administered at the initial dosage of about 0.1 μg/kg to about 1000 μg/kg daily and adjusted over time. A daily dose range of about 1 μg/kg to about 500 μg/kg, or about 10 μg/kg to about 100 μg/kg, or about 30 μg/kg to about 50 ug/kg can be used. The dosage is varied depending upon the requirements of the patient, the severity of the condition being treated, and the route of administration. For example, for injection of Klotho polypeptide, the effective dose is typically in the range of 10-100 μg/kg, while for direct delivery to the central nervous system (CNS), the effective dosage is lower, e.g., 5-30 μg/kg. For oral administration, the effective dose is higher, e.g., in the range of 50-10,000 μg/kg (e.g., 100 μg/kg-2 mg/kg). The dose is chosen in order to provide effective therapy for the patient. The dose may be repeated at an appropriate frequency which may be in the range of once or twice per day, once or twice per week to once every three months, depending on the pharmacokinetics of the Klotho polypeptide composition (e.g., half-life in the circulation) and the pharmacodynamic response (e.g., the duration of the therapeutic effect).

Administration can be periodic. Depending on the route of administration, the dose can be administered, e.g., once every 1, 3, 5, 7, 10, 14, 21, or 28 days or longer (e.g., once every 2, 3, 4, or 6 months). In some cases, administration is more frequent, e.g., 2 or 3 times per day. The patient can be monitored to adjust the dosage and frequency of administration depending on therapeutic progress and any adverse side effects, as will be recognized by one of skill in the art.

Dosages can be empirically determined considering the type and severity of cognitive condition diagnosed in a particular patient. The dose administered to a patient, in the context of the present disclosure, should be sufficient to affect a beneficial therapeutic response in the patient over time. The size of the dose will also be determined by the existence, nature, and extent of any adverse side-effects that accompany the administration of any particular composition in a particular patient, as will be recognized by the skilled practitioner.

In some embodiments, the Klotho polypeptide composition is administered to an (e.g., human) individual having at least normal cognitive function. As described herein, it has been surprisingly discovered that not only can Klotho improve cognition in individuals with impaired cognition, Klotho can also improve cognition of individuals with at least normal cognition. Thus in some embodiments, the individual receiving the Klotho polypeptide composition begins initially with at least normal cognition and following administration of the Klotho polypeptide composition attains improved cognition compared to the initial level of cognition. The level of cognition of an individual can be determined as is known in the art. Normal cognitive functions are determined by scores from sets of cognitive tests that are compiled into global cognitive scores, as described in Dubal D B et al. (2014) Cell Reports 7:1065-1076. Such cognition tests include tests of executive function and working memory such as Trails A and Trails B (Dubal D B et al. (2014) Cell Reports 7:1065-1076). In some embodiments, administration of Klotho results in an improvement of cognition (whether initially at least normal or impaired), by at least 5%, 10%, 20% or more.

In some embodiments, administration results in improved motor function. In some embodiments, the Klotho polypeptide composition is administered to an (e.g., human) individual having impaired motor function. For example, in some embodiments, the individual has stroke to the brain or spinal cord (ischemic or hemorrhagic), neurodegenerative disease (Parkinson's disease, Lewy body dementia, multiple system atrophy, amyotropic lateral sclerosis, prion disorder, Huntington's disease, supranuclear palsy), Parkinsonism, traumatic brain injury, neuroinfectious brain lesions, multiple sclerosis and related autoimmune and demyelinating disease, spinal cord lesions (compressive, infectious, toxic or metabolic, autoimmune, oncologic), brain tumor, epilepsy, paraneoplastic disorder, neurodevelopmental disorder (mitochondrial, autosomal genetic), muscle disease (polymyositis, dermatomyositis, inclusion body myositis, infectious, endocrine, metabolic, toxic, congenital myopathy, congenital muscular dystrophy, hereditary), neuropathies (Guillain-Barre syndrome, axonal and demyelinating, diabetic, toxic, metabolic, infectious, critical illness, entrapment), tick paralysis, myasthenia gravis, and spinal muscular atrophy. Changes in motor function can be assayed as known in the art. Exemplary motor function assays include but are not limited to electromyogram and nerve conduction studies, direct or device-assisted clinical testing of strength, tone, and muscle bulk, reflex examination, coordination examination, and gait analysis. Assays for testing etiologies causing deficits of motor function include but are not limited to magnetic resonance imaging of the central nervous system, muscle biopsy, nerve biopsy, and laboratory studies.

Thus in some embodiments, additional administration is dependent on patient progress, e.g., the patient is monitored between administrations. For example, after the first administration or round of administrations, the patient can be monitored for cognitive ability or for side effects, e.g., weakness, dizziness, nausea, etc.

In some embodiments, the individual has a chronic condition, so that klotho is administered over an indefinite period, e.g., for the lifetime of the patient. In such cases, administration is typically periodic. Diseases that are considered long-term or chronic include, but are not limited to Alzheimer's disease, Parkinson's disease, Huntington's disease, and cognitive decline associated with hypertension and heart disease.

In some embodiments, the Klotho polypeptide is linked to a stabilizing moiety such as PEG, glycosylation, or a liposome or other nanocarrier. U.S. Pat. Nos. 4,732,863 and 7,892,554 and Chattopadhyay et al. (2010) Mol Pharm 7:2194 describe methods for attaching a polypeptide to PEG, PEG derivatives, and nanoparticles (e.g., liposomes). Liposomes containing phosphatidyl-ethanolamine (PE) can be prepared by established procedures as described herein. The inclusion of PE provides an active functional site on the liposomal surface for attachment. In some embodiments, the Klotho polypeptide is linked to an affinity tag, e.g., a histidine tag (e.g., 4-16 histidine residues), streptavidin, or an antibody target.

The Klotho polypeptide can also be formulated as a sustained-release preparation (e.g., in a semi-permeable matrices of solid hydrophobic polymers (e.g., polyesters, hydrogels (for example, poly (2-hydroxyethyl-methacrylate), or poly (vinylalcohol)), polylactides. The Klotho polypeptide can be entrapped in a nanoparticle prepared, for example, by coacervation techniques or by interfacial polymerization, for example, hydroxymethylcellulose or gelatin microcapsules and poly-(methylmethacylate) microcapsules, respectively, in colloidal drug delivery systems (for example, liposomes, albumin microspheres, microemulsions, nanoparticles and nanocapsules) or in macroemulsions.

In some embodiments, the Klotho polypeptide is labeled, e.g., for tracking in the body or ex vivo. The Klotho polypeptide can be labeled any diagnostic agent known in the art, as provided, for example, in the following references: Armstrong et al., Diagnostic Imaging, 5$^{th}$ Ed., Blackwell Publishing (2004); Torchilin, V. P., Ed., Targeted Delivery of Imaging Agents, CRC Press (1995); Vallabhajosula, S., Molecular Imaging: Radiopharmaceuticals for PET and SPECT, Springer (2009). The diagnostic agent can be detected by a variety of ways, including as an agent providing and/or enhancing a detectable signal. Detectable signals include, but are not limited to, gamma-emitting, radioactive, echogenic, optical, fluorescent, absorptive, magnetic, or tomography signals. Techniques for imaging the diagnostic agent can include, but are not limited to, single photon emission computed tomography (SPECT), magnetic resonance imaging (MRI), optical imaging, positron emission tomography (PET), computed tomography (CT), x-ray imaging, gamma ray imaging, and the like. The terms "detectable agent," "detectable moiety," "label," "imaging agent," and like terms are used synonymously herein.

In some embodiments, the label can include optical agents such as fluorescent agents, phosphorescent agents, chemiluminescent agents, and the like. Numerous agents (e.g., dyes, probes, labels, or indicators) are known in the art and can be used in the present invention. (See, e.g., Invitrogen, The Handbook—A Guide to Fluorescent Probes and Labeling Technologies, Tenth Edition (2005)). Fluorescent agents can include a variety of organic and/or inorganic small molecules or a variety of fluorescent proteins and derivatives thereof. For example, fluorescent agents can include but are not limited to cyanines, phthalocyanines, porphyrins, indocyanines, rhodamines, phenoxazines, phenylxanthenes, phenothiazines, phenoselenazines, fluoresceins, benzoporphyrins, squaraines, dipyrrolo pyrimidones, tetracenes, quinolines, pyrazines, corrins, croconiums, acridones, phenanthridines, rhodamines, acridines, anthraquinones, chalcogenopyrylium analogues, chlorins, naphthalocyanines, methine dyes, indolenium dyes, azo compounds, azulenes, azaazulenes, triphenyl methane dyes, indoles, benzoindoles, indocarbocyanines, benzoindocarbocyanines, and BODIPY™ derivatives. Fluorescent dyes are discussed, for example, in U.S. Pat. Nos. 4,452,720, 5,227,487, and 5,543,295.

The label can also be a radioisotope, e.g., radionuclides that emit gamma rays, positrons, beta and alpha particles, and X-rays. Suitable radionuclides include but are not limited to $^{225}$Ac, $^{72}$As, $^{211}$At, $^{11}$B, $^{128}$Ba, $^{212}$Bi, $^{75}$Br, $^{77}$Br, $^{14}$C, $^{109}$Cd, $^{62}$Cu, $^{64}$Cu, $^{67}$Cu, $^{18}$F, $^{67}$Ga, $^{68}$Ga, $^{3}$H, $^{166}$Ho, $^{123}$I, $^{124}$I, $^{125}$I, $^{130}$I, $^{131}$I, $^{111}$In, $^{177}$Lu, $^{13}$N, $^{15}$O, $^{32}$P, $^{33}$P, $^{212}$Ph, $^{103}$Pd, $^{186}$Re, $^{188}$Re, $^{47}$Sc, $^{153}$Sm $^{89}$Sr, $^{99m}$Tc, $^{88}$Y and $^{90}$Y. In some embodiments, radioactive agents can include $^{111}$In-DTPA, $^{99m}$Tc(CO)$_3$-DTPA, 99mTc(CO)$_3$-ENPy2, $^{62/64/67}$Cu-TETA, $^{99m}$Tc(CO)$_3$-IDA, and $^{99m}$Tc(CO)$_3$triamines (cyclic or linear). In some embodiments, the agents can include DOTA and its various analogs with $^{111}$In, $^{177}$Lu, $^{153}$Sm, $^{88/90}$Y, $^{62/64/67}$Cu, or $^{67/68}$Ga. In some embodiments, a nanoparticle can be labeled by incorporation of lipids attached to chelates, such as DTPA-lipid, as provided in the following references: Phillips et al., *Wiley Interdisciplinary Reviews: Nanomedicine and Nanobiotechnology*, 1(1): 69-83 (2008); Torchilin, V. P. & Weissig, V., Eds. *Liposomes* 2nd Ed.: Oxford Univ. Press (2003); Elbayoumi, T. A. & Torchilin, V. P., *Eur. J. Nucl. Med. Mol. Imaging* 33:1196-1205 (2006); Mougin-Degraef, M. et al., *Int'l J. Pharmaceutics* 344:110-117 (2007).

In some embodiments, the diagnostic agent can be associated with a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Secondary binding ligands include, e.g., biotin and avidin or streptavidin compounds as known in the art.

V. Cognitive Conditions and Disorders

Klotho polypeptides (and functional variants and fragments thereof) can be administered to improve cognition for a number of conditions and situations. This includes treatment of individuals with lower than normal or declining cognitive ability, or prophylactic treatment of individuals in need of improved or increased cognitive ability.

Klotho polypeptides (and functional variants and fragments thereof) can be used to prevent or reduce cognitive decline associated with aging, e.g. in individuals 50 years of age or older, or upon initial signs of cognitive decline.

Klotho polypeptides (and functional variants and fragments thereof) can also be used to treat individuals with age-related, non-age related, or disease related conditions including, but not limited to:

Neurodegenerative diseases and dementia: Alzheimer's disease, Parkinson's disease, Huntington's disease, frontotemporal dementia, progressive supranuclear palsy, corticobasalar degeneration, mild cognitive impairment, vascular dementia, Lewy body dementia, amyotrophic lateral sclerosis, prion disorder, HIV-related dementia;

Mental or mood disorders: depression, schizophrenia, attention deficit/hyperactivity disorder, autism spectrum disorder, intellectual disability, a mood disorder, and a psychotic disorder;

Childhood neurodevelopmental syndromes and brain tumors: X-linked mental disability or retardation, astrocytoma, ependymoma, medulloblastoma, oligodendroglioma;

Genetic syndromes affecting learning: Down's syndrome, Angelman's syndrome, Rett's syndrome;

Metabolic disorders affecting cognition: phenylketonuria, Lesch-Nyhan, galactosemia, and adrenoleukodystrophy;

Cognitive decline associated with chemotherapy and/or radiation therapy; and

Additional conditions and disorders: pain-associated cognitive effects, traumatic brain injury, stroke, multiple sclerosis, neuroautoimmune disease, epilepsy, delirium, paraneoplastic disorder, developmental delay, and leukodystrophies.

Klotho polypeptides (and functional variants and fragments thereof) can be also be administered to provide increased cognition for individuals desiring improved cognition, e.g., individuals exposed to stress, sleep deprivation, or jet lag, or for individuals requiring superior cognitive function, such as surgeons, air-traffic controllers, and military personal. In such cases, the klotho polypeptide composition can be administered 2-24 hours before the desired effect, which can last about 3-5 days for working memory and about 2 weeks for spatial memory.

Cognitive ability can be measured using any method known in the art, e.g., for testing memory, language ability, executive functions, visuospatial function, dementia, or multi-parameter neuropsychological abilities. In some embodiments, Klotho administration results in at least a 1%, 2%, 5%, 7%, 10%, 15%, 20%, 30%, 50%, or greater improvement in score on a standard cognitive ability test (e.g., measured 1-3 days after administration). In some embodiments, the testing is carried out more than once for an individual, e.g., one or more time over the course of treatment with Klotho.

For example, standard tests for memory and learning can be applied, e.g., to determine semantic, episodic, procedural, priming, and/or working (i.e., short term) memory. Common tests include Cambridge prospective memory test (CAM-PROMPT), memory assessment scales (MAS), Rey auditory verbal learning test, Rivermead behavioral memory test, Test of memory and learning (TOMAL), Wechsler memory scale (WMS), and Test of memory malingering (TOMM). Tests for language functions include, e.g., Boston Diagnostic Aphasia Examination (BDAE), Comprehensive aphasia test (CAT), and Multilingual aphasia examination (MAE).

Executive function (e.g., problem solving, planning, organization, inhibitory control) can be tested using Behavioral assessment of dysexecutive syndrome (BADS), CNS vital signs (Brief Core Battery), Controlled oral word association test (COWAT), Delis-Kaplan Executive Function System (D-KEFS), Digit vigilance test, Kaplan Baycrest neurocognitive assessment (KBNA), Hayling and Brixton tests, Tests of variables of attention (TOVA), Wisconsin card sorting test (WCST), or Test of everyday attention (TEA). Visuospatial ability (e.g., visual perception, construction and integration) can be tested using the Clock Test, Hooper visual organization task (VOT), or Rey-Osterrieth complex figure tests. Dementia can be quantified using the clinical dementia rating or dementia rating scale.

Multi-parameter tests for neuropsychological function (e.g., cognitive function) include but are not limited to the Barcelona neuropsychological test (BNT), Cambridge neuropsychological test automated battery (CANTAB), Cognistat, Cognitive assessment screening instrument (CAST), Cognitive function scanner (CFS), Dean-Woodcock neuropsychology assessment system (DWNAS), General practitional assessment of cognition (GPCOG) Mini mental state examination (MMSE), NEPSY, or the CDR computerized assessment system.

Alternatively, cognition can be determined using structural or molecular proxies for cognitive activity, e.g., compared over time to detect changes. Cognitive changes can be detected, e.g., by observing changes to brain structure, connectivity, activation, inhibition, or synaptic plasticity, e.g., by MRI, fMRI, EEG, TMS and TES, and/or any combination of these. In some embodiments, brain activity is observed. In some embodiments, Klotho administration results in a 1.5-fold, 2-fold, 5-fold, 7-fold, 10-fold, or greater increase in brain activity (e.g., measured 1-3 days after administration). Molecular proxies for improved cognition include, but are not limited to: increased levels of GluN2B, increased GluN2B synaptic localization, increased NMDA receptor activation, and/or increased c-fos activation in the brain. These measures are particularly relevant to cognition. Such method can include, e.g., obtaining a sample of neuronal tissue or CSF from an individual and using standard assays to determine gene expression or activation.

Similarly, in mice and other non-human animals, cognitive ability can be tested with measures of executive function (working memory, attention, processing speed, set shifting), visiospatial learning and memory, object memory, pattern recognition, fear memory, passive avoidance memory, habituation, and novel object recognition, for example. Common tests include but are not limited to the Morris water maze, Barnes maze, radial arm water maze, y-maze, T-maze, and open field habituation. Brain imaging techniques are similarly applicable.

VI. Examples

Example 1

A. Materials and Methods

Mice. All mice were on a C57BL/6J background and were kept on a 12-h light/dark cycle with ad libitum access to food (Picolab Rodent Diet 20, Labdiet) and water. The standard housing group was five mice per cage except for single housing during water maze studies. All cognitive and behavioral studies were carried out during the light cycle. All studies were conducted in a blinded manner.

Treatments. Vehicle or klotho (recombinant mouse klotho, amino acids 35-982, with a C-terminal His tag, R&D Systems) was injected intraperitoneally (i.p.) before behavioral testing of mice.

Morris water maze cognitive behavior test. Water maze studies were carried out as described in Dubal et al. (2014) *Cell Reports* 7:1065; Dubal et al. (2015) *Journal of Neuroscience* 35:2358. Mice were treated with either vehicle or klotho (10 µg/kg) i.p. 4 h prior to testing daily for 5 days. Briefly, mice were tested in a pool (diameter, 122 cm) with white, opaque water (21°±1° C.). A square, 14-cm2 platform was 2 cm below the surface. Before hidden platform training, mice underwent two pre-training trials by swimming through a channel to mount a hidden platform. Over the course of hidden platform training, the platform location stayed consistent while the drop location was varied between trials. Mice underwent two training sessions, consisting of two trials of 60 s each, daily for four days. For the probe trial testing, the platform was removed and the mice were allowed to swim for 60 s. After 1 h and 24 h probe trials, mice were tested for their ability to find a visible platform marked with a cue (15-cm pole on the platform) over two sessions. As part of the studies, swim velocities were also recorded.

Y-maze cognitive behavior test. Y-maze studies were carried out as described in Dubal et al. (2014) *Cell Reports* 7:1065. Mice were treated with either vehicle or klotho (10 m/kg) i.p. 18 h prior to testing. Briefly, mice were acclimated to the room 30 min prior to testing. Then, mice were placed in one arm of the Y-maze (three identical arms, 120° apart) and explored for 4 min. Arm entries were recorded and an alternation was noted any time the mouse entered each of the three arms in successive arm entries; chance alternation was 22%. The apparatus was cleaned with 70% alcohol between testing sessions. Percent alternation was calculated from recorded data.

B. Systemic Klotho Delivery Enhances Working Memory in Young Mice

Figure 1A:
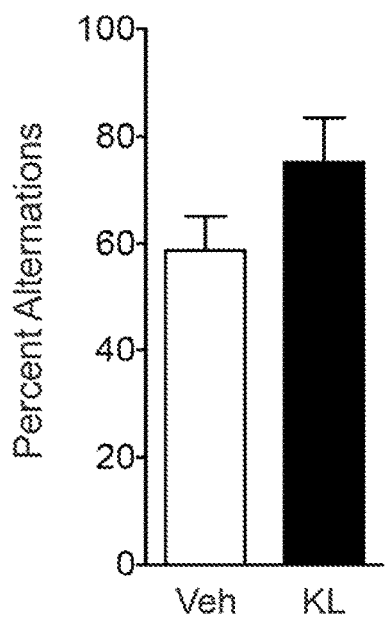
FIG. 1A-J. Klotho delivery enhances cognition in mice. Mice were tested in cognitive tasks following i.p. delivery of vehicle (Veh) or recombinant mouse klotho (KL) (10 µg/kg) (age 4 months). Data are mean±SEM.

To investigate whether therapeutic delivery of klotho can enhance cognition, we injected mice with recombinant klotho (i.p.) and 18 h later, tested working memory in the Y-maze. Compared to vehicle-treated mice, klotho-treated mice showed more alternations, indicating superior working memory (FIG. 1A). Thus, systemic klotho delivery enhanced working memory, a process that involves frontal cortical brain regions.

C. Systemic Klotho Delivery Enhances Spatial Learning in Young Mice

Figure 1B:
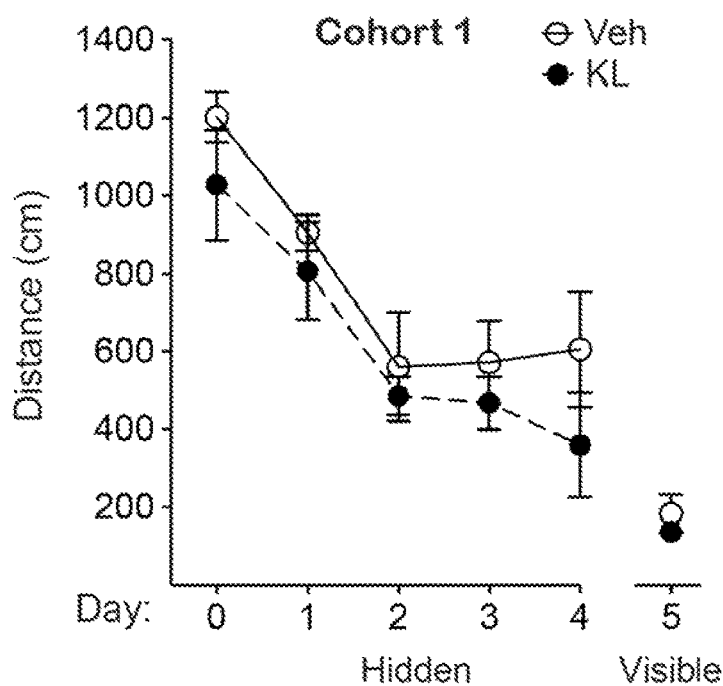
Figure 1C:
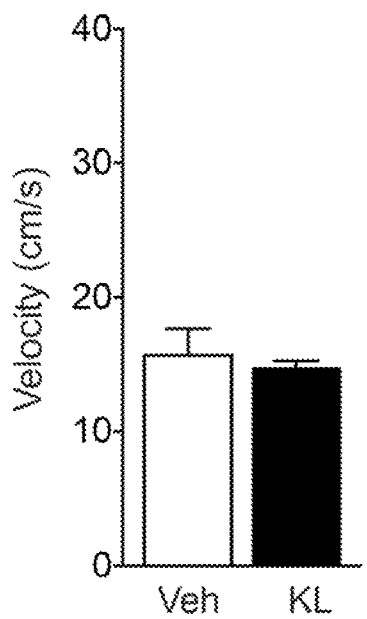
Figure 1D:
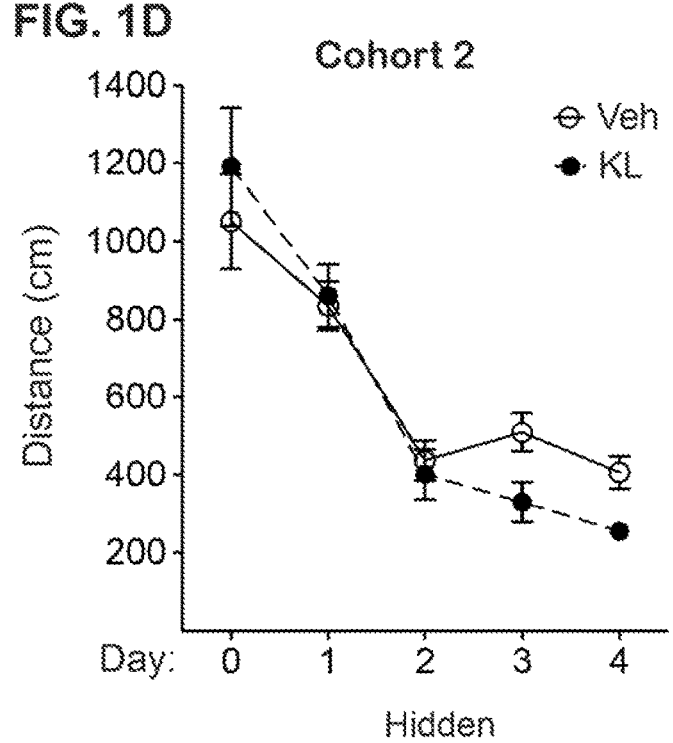

We next tested whether klotho treatment enhances spatial learning in the Morris water maze. We injected mice with recombinant klotho (i.p.) 4 h prior to testing daily for five days in a group of mice (Cohort 1). Compared to vehicle-treated mice, klotho-treated mice performed better in spatial learning of the hidden platform location (FIG. 1B). Both groups swam at equal speeds (FIG. 1C). In an independent group of mice (Cohort 2), we injected recombinant klotho (i.p.) 18 h prior to testing daily. Again, compared to vehicle-treated mice, klotho-treated mice performed better in spatial learning (FIG. 1D). Thus, systemic klotho delivery enhanced spatial learning, a process that involves frontal cortical and hippocampal brain regions.

D. Systemic Klotho Delivery Enhances Spatial Memory in Young Mice

Figure 1E:
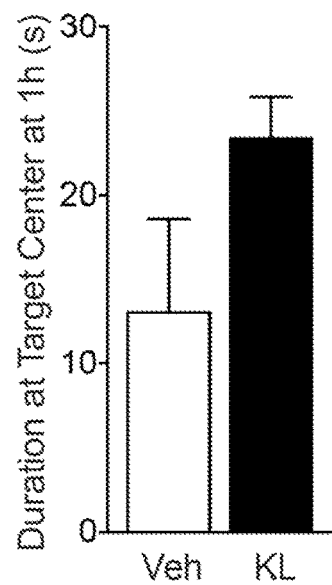
Figure 1F:
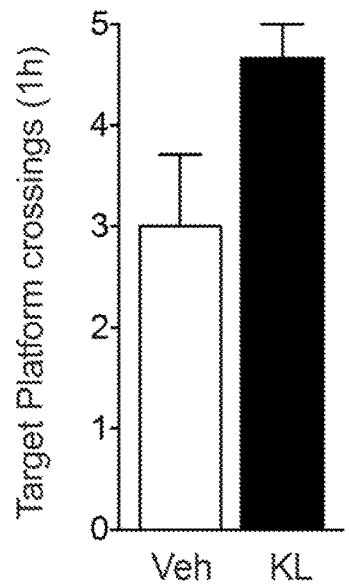
Figure 1G:
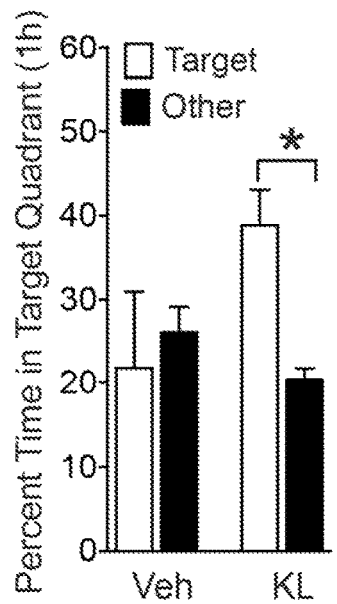
Figure 1H:
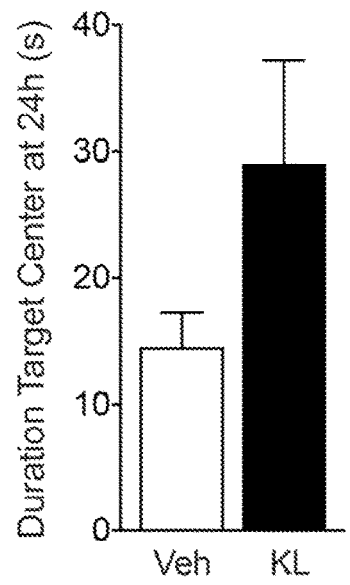
Figure 1I:
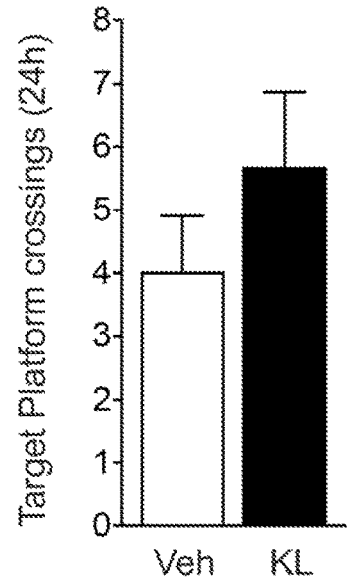
Figure 1J:
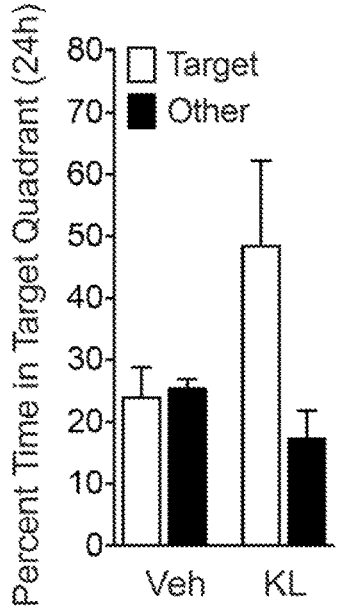

To determine whether klotho treatment can enhance spatial memory, we removed the platform and performed probe testing following hidden training in the Morris water maze. In probe trials of Cohort 1, spatial memory retention was assessed by measuring the affinity of mice for the target area. In probe testing at 1 h, klotho-treated mice spent more time at the target center (FIG. 1E), showed increased frequency of crossing the target (FIG. 1F), and increased time in the target quadrant (FIG. 1G), compared to vehicle-treated controls. In probe testing at 24 h, klotho-treated mice continued to show more center duration (FIG. 1H), crossing frequency (FIG. 1I), and percent time in the target quadrant (FIG. 1J), compared to vehicle-treated mice. Thus, systemic klotho delivery enhanced spatial memory, a process that engages hippocampal brain regions.

The data show that systemic delivery of klotho enhances normal cognition in mice. Klotho treatment improved learning and memory in multiple tests and measures including working memory, spatial learning, and spatial memory. These findings provide a direct therapeutic application for boosting cognitive functions, a therapy that is relevant, but not limited to, cognitive enhancement of the normal brain and cognitive dysfunction due to normal aging, numerous neurodegenerative, neurologic, and psychiatric diseases, childhood developmental syndromes, traumatic brain injury, and stress.

Example 2

Methods.

Mice. All mice were on a C57BL/6J background and were kept on a 12-h light/dark cycle with ad libitum access to food (Picolab Rodent Diet 20, Labdiet) and water. The standard housing group was five mice per cage except for single housing during water maze studies. All motor, cognitive and behavioral studies were carried out during the light cycle. All studies were conducted in a blinded manner.

Aged mice (18 months) were obtained from the NIH aging colony and were used in experiments. Transgenic mice that model human neurodegenerative diseases related to α-synuclein toxicity were utilized in experiments; these mice express full length human α-synuclein from the mouse Thy-1 promoter (Rockenstein E, et al. (2002) *J Neurosci Res* 68:568-578) and exhibit motor, cognitive and behavioral deficits. Increased expression of the human α-synuclein protein contributes to several neurodegenerative diseases in the human condition including, but not limited to, Parkinson's disease (PD), Alzheimer's disease (AD), Lewy body dementia (LBD), and multiple system atrophy (MSA).

Treatments. Vehicle or α-klotho (recombinant mouse α-klotho, amino acids 35-982, with a C-terminal His tag, R&D Systems) was injected intraperitoneally (i.p.) before behavioral testing of mice as indicated. All animal studies were approved by the Institutional Animal Care and Use Committee of the University of California, San Francisco and conducted in compliance with NIH guidelines.

Cognitive and Motor Behavior

Morris water maze. Water maze studies were carried out as described (Zarei M, et al. (2013) *J Neurol Neurosurg Psychiatry* 84:875-881; Dubal D B et al. (2014) *Cell Reports* 7:1065-1076). Mice were treated with either vehicle or klotho (10 μg/kg) i.p. 4 h prior to testing daily for 5 days. Briefly, mice were tested in a pool (diameter, 122 cm) with white, opaque water (21°±1° C.). A square, 14-cm2 platform was 2 cm below the surface. Before hidden platform training, mice underwent two pre-training trials by swimming through a channel to mount a hidden platform. Over the course of hidden platform training, the platform location stayed consistent while the drop location was varied between trials. Mice underwent two training sessions, consisting of two trials of 60 s each, daily for four days. For the probe trial testing, the platform was removed and the mice were allowed to swim for 60 s. After 1 h and 24 h probe trials, mice were tested for their ability to find a visible platform marked with a cue (15-cm pole on the platform) over two sessions. As part of the studies, swim velocities were also recorded.

Y-maze. Y-maze studies were carried out as described (Dubal D B et al. (2014) *Cell Reports* 7:1065-1076). Mice were treated with either vehicle or klotho (10 μg/kg) i.p. 18 h prior to testing. Briefly, mice were acclimated to the room 30 min prior to testing. Then, mice were placed in one arm of the Y-maze (three identical arms, 120° apart) and explored for 4 min. Arm entries were recorded and an alternation was noted any time the mouse entered each of the three arms in successive arm entries; chance alternation was 22%. The apparatus was cleaned with 70% alcohol between testing sessions. Percent alternations was calculated from recorded data.

Large Y-maze. Large Y-maze studies were performed as described (Dellu F, et al. (1992) *Brain Res* 588:132-139) with minor modifications. The large Y-maze apparatus consists of three identical arms, 120° apart, with a distinct and different visual cue at the back end of two arms; the third arm without a visual cue is the start arm. Prior to training or testing, mice were acclimated to the dimly lit room for 60 minutes. During training, one arm with a visual cue was blocked with a solid divider and mice were placed at the end of the start arm. Mice were allowed to explore the open arm for five minutes and then returned to their cages. The open arm used in training (the familiar arm) was counterbalanced throughout the cohort testing. 16 hours after training, mice underwent testing. During testing, the divider was removed. Mice were placed in the start arm and allowed to explore the arms with novel and familiar visual cues (novel arm and familiar arm) for 5 minutes. Number of entries and duration of time spent in the novel and familiar arms was recorded and measured. The ratio of novel to familiar arm entries or duration was calculated to assess spatial and working memory. The apparatus was cleaned with 70% alcohol between sessions.

Rota Rod. Mice were acclimated to the room 60 minutes prior to each session. Five mice were simultaneously put on the rotating rod (Rota Rod, Med Associates Inc, VT) at a constant speed of 16 rpm for a maximum of 300 seconds. Latency to fall was recorded in each trial. Three trials were performed consecutively with a 10 minute rest between trials. The apparatus was cleaned with 70% alcohol between testing sessions.

Open field. Total activity in the open field was measured as described (Dubal D B, et al. (2015) *J Neurosci* 35:2358-2371) with an automated Flex-Field/Open Field Photobeam Activity System (San Diego Instruments, San Diego, Calif.). Mice were acclimated to the testing room for 30 minute and then tested in a clear plastic chamber (41×30 cm) for 5 min, with two photobeam arrays measuring movements. The apparatus was cleaned with 70% alcohol between testing sessions.

Results.

Figure 2A:
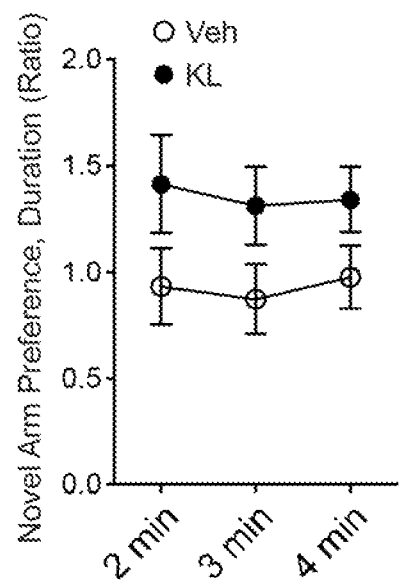
FIG. 2A-B. Acute delivery of klotho enhances cognition in aged mice. Mice were tested for spatial and working memory in the large Y-Maze following i.p. delivery of vehicle (Veh) or recombinant mouse klotho (KL) (10 µg/kg) 24 hours prior to training (n=8-9 mice per experimental group, sex-balanced groups, age 18 months, from NIH colony of aging mice). 18 hours after training, mice underwent testing and duration of time spent in the novel arm and the familiar arm was measured during exploration of the maze.
Figure 2B:
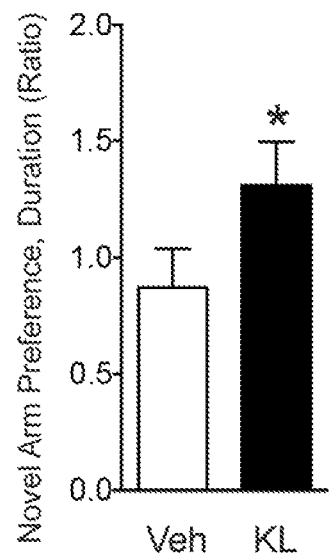

Systemic klotho delivery enhances cognition in aged mice. To determine whether therapeutic delivery of klotho can enhance cognition in aged mice, we injected mice with recombinant klotho (i.p., 10 μg/kg) once and then trained them for a task to measure working and spatial memory in the large Y-maze 24 h later. Then, 18 h following training (42 h after klotho delivery), mice underwent testing. At baseline, and without klotho treatment, the aged mice did not show novel arm preference, indicating a cognitive deficit. Compared to vehicle-treated mice, klotho-treated mice showed a persistent preference for the novel arm largely throughout exploration (FIG. 2A,B), indicating better cognition that involves frontal and hippocampal brain regions. These data show that klotho enhances cognition in mice with age-induced cognitive deficits. These data suggest that therapeutic delivery of klotho enhances cognition in the aging brain.

Systemic klotho delivery enhances cognition in a long-lasting manner. To determine whether therapeutic delivery of klotho can induce long-lasting cognitive enhancement, in a manner that extends beyond its half-life of 7 hours (Hu M C, et al. (2015) *J Am Soc Nephrol.*), we tested young mice approximately two weeks after 5 days of daily klotho treatment and cognitive testing (i.p., 0.5 or 2.5 μg/kg). As expected, vehicle-treated mice did not show preference for the novel arm, indicating a loss of memory for the visual cue after two weeks. In contrast, klotho-treated mice showed a clear preference for the novel arm of the maze—even two weeks after the last treatment and in a dose-dependent manner (FIG. 3). These data indicate that klotho-mediated cognitive enhancement in normal, young mice was long-lasting and extended at least two weeks beyond its half-life. These data suggest that therapeutic delivery of klotho induces organizational changes in the brain that enhance neural function.

Systemic klotho delivery improves cognitive dysfunction in mice that model neurodegenerative disease. We next tested whether acute, therapeutic delivery of klotho can improve existing cognitive deficits in a mouse model of neurodegenerative disease. In this well-characterized model of disease, mice express human α-synuclein (hSYN), a pathogenic protein that causes cognitive and motor deficits and contributes to Parkinson's disease, Alzheimer's disease, Lewy body dementia, and multiple system atrophy. In these mice, cognitive function was assessed in the large-Y maze. This task is optimal since it utilizes the mouse's natural tendency to explore, avoids testing-induced stressors, and is not affected by motor difficulties that limit other tests (such as inability to swim appropriately in a water maze). Compared to nontransgenic (NTG) mice, hSYN mice showed decreased preference for the novel arm, as shown by decreased duration (FIG. 4A). Remarkably, klotho treatment of hSYN mice (i.p., 2.5 µg/kg,) increased novel arm preference (FIG. 4A,B), indicating acute and therapeutic cognitive improvement. There was an overall effect of klotho treatment in enhancing memory as indicated by increasing novel arm preference (Two-way ANOVA KL effect p<0.05) (FIG. 4B). These data suggest that therapeutic delivery of klotho can reverse or improve cognitive deficits caused by α-synuclein toxicity in neurodegenerative diseases. Of note, klotho-mediated cognitive enhancement could contribute to improved motor learning.

Systemic klotho delivery improves early motor dysfunction in mice that model neurodegenerative disease. Since α-synculein toxicity induces deficits in motor function, a major clinical problem in neurodegenerative diseases, we tested whether therapeutic delivery of klotho can improve this key measure in hSYN mice. Motor function was assessed on a spinning rod, the Rota rod. Compared to NTG mice, hSYN mice showed decreased motor function (FIG. 5). Remarkably, klotho treatment (i.p., 2.5 µg/kg) of hSYN mice acutely increased motor function, as shown by longer latency on the spinning rod (FIG. 5). These data indicate that klotho treatment acutely improves early motor function in hSYN mice. These data suggest that therapeutic delivery of klotho can improve deficits related to motor problems caused by α-synuclein toxicity in neurodegenerative diseases.

Systemic klotho delivery does not alter total movements or activity of mice. To examine whether klotho delivery alters total movements and activity of mice, we examined mouse exploration of an open field. Total movements did not differ between Veh- or KL-treated (i.p., 2.5 µg/kg) mice (FIG. 6). These data suggest that the therapeutic effects of klotho are specific to cognitive and motor functions and are not influenced by non-specific actions such as hyperactivity.

Discussion

Our data show that systemic delivery of klotho, which does not cross the blood brain barrier, enhances normal cognition in young mice in a manner that is long-lasting, improves cognitive deficits in normal young mice and in aging mice; it also improves cognitive and motor deficits in transgenic mice that model major neurodegenerative diseases such as Alzheimer's disease, Parkinson's disease, Lewy body dementia, and multiple system atrophy.

These findings provide a direct therapeutic application for boosting cognitive functions in the normal brain and improving brain function in aging and neurodegenerative disease. This therapeutic application is also relevant, but not limited to, cognitive dysfunction due to numerous neurologic, and psychiatric diseases, childhood developmental syndromes, traumatic brain injury, and stress.

Our data show that:
1. Systemic administration of mouse recombinant klotho forms enhance normal cognition across the lifespan from young (2-7 mos) to aged (18 mos) male and female mice.
2. Systemic klotho therapy is effective in enhancing cognition when given from 4 hours to 16 days prior to testing. The cognitive-enhancing effects last for at least two weeks following extensive cognitive training.
3. Systemic doses of mouse klotho between 0.5 µg/kg and 10 µg/kg enhance cognition in conditions tested.
4. Systemic therapy with recombinant klotho enhances cognition in a mouse model of neurodegenerative disease relevant to, but not limited to, Alzheimer's disease, Parkinson's disease, Lewy body dementia, and multiple system atrophy.
5. In addition to improving cognitive deficits in a mouse model of neurodegenerative disease, klotho therapy also improved early motor function.
6. The therapeutic effects of klotho on enhancing cognition extend far beyond its half-life of approximately 7 hours.
7. The therapeutic effects of klotho appear specific to cognitive and motor functions and are not influenced by non-specific actions such as hyperactivity.

The above examples are provided to illustrate the invention but not to limit its scope. Other variants of the invention will be readily apparent to one of ordinary skill in the art and are encompassed by the appended claims. All publications, databases, internet sources, patents, patent applications, and accession numbers cited herein are hereby incorporated by reference in their entireties for all purposes.

```
VII. Informal sequence listing
SEQ ID NO: 1: Human Klotho Protein
         10          20          30          40          50
    MPASAPPRRP  RPPPPSLSLL  LVLLGLGGRR  LRAEPGDGAQ  TWARFSRPPA 60          70          80          90         100
    PEAAGLFQGT  FPDGFLWAVG  SAAYQTEGGW  QQHGKGASIW  DTFTHHPLAP 110         120         130         140         150
    PGDSRNASLP  LGAPSPLQPA  TGDVASDSYN  NVFRDTEALR  ELGVTHYRFS 160         170         180         190         200
    ISWARVLPNG  SAGVPNREGL  RYYRRLLERL  RELGVQPVVT  LYHWDLPQRL
```

-continued

```
        210        220        230        240        250
QDAYGGWANR ALADHFRDYA ELCFRHFGGQ VKYWITIDNP YVVAWHGYAT 260        270        280        290        300
GRLAPGIRGS PRLGYLVAHN LLAHAKVWH  LYNTSFRPTQ GGQVSIALSS 310        320        330        340        350
HWINPRRMTD HSIKECQKSL DFVLGWFAKP VFIDGDYPES MKNNLSSILP 360        370        380        390        400
DFTESEKKFI KGTADFFALC FGPTLSFQLL DPHMKFRQLE SPNLRQLLSW 410        420        430        440        450
IDLEFNHPQI FIVENGWFVS GTTKRDDAKY MYYLKKFIME TLKAIKLDGV 460        470        480        490        500
DVIGYTAWSL MDGFEWHRGY SIRRGLFYVD FLSQDKMLLP KSSALFYQKL 510        520        530        540        550
IEKNGFPPLP ENQPLEGTFP CDFAWGVVDN YIQVDTTLSQ FTDLNVYLWD 560        570        580        590        600
VHHSKRLIKV DGVVTKKRKS YCVDFAAIQP QIALLQEMHV THFRFSLDWA 610        620        630        640        650
LILPLGNQSQ VNHTILQYYR CMASELVRVN ITPVVALWQP MAPNQGLPRL 660        670        680        690        700
LARQGAWENP YTALAFAEYA RLCFQELGHH VKLWITMNEP YTRNMTYSAG 710        720        730        740        750
HNLLKAHALA WHVYNEKFRH AQNGKISIAL QADWIEPACP FSQKDKEVAE 760        770        780        790        800
RVLEFDIGWL AEPIFGSGDY PWVMRDWLNQ RNNFLLPYFT EDEKKLIQGT 810        820        830        840        850
FDFLALSHYT TILVDSEKED PIKYNDYLEV QEMTDITWLN SPSQVAVVPW 860        870        880        890        900
GLRKVLNWLK FKYGDLPMYI ISNGIDDGLH AEDDQLRVYY MQNYINEALK 910        920        930        940        950
AHILDGINLC GYFAYSFNDR TAPRFGLYRY AADQFEPKAS MKHYRKIIDS 960        970        980        990        1000
NGFPGPETLE RFCPEEFTVC TECSFFHTRK SLLAFIAFLF FASIISLSLI

1010
FYYSKKGRRS YK
```

---

What is claimed is:

1. A method for improving cognitive function or inhibiting cognitive decline in an individual in need thereof, comprising administering to the individual an effective amount of a polypeptide that includes an amino acid sequence that is at least 95% identical to the sequence of the KL1 domain contained in SEQ. ID NO:1, with the proviso that the polypeptide is not a fusion protein that also contains a fibroblast growth factor (FGF),
wherein the administering is systemic or peripheral, thereby improving cognitive function or inhibiting cognitive decline in the individual.

2. A method for improving cognitive function or inhibiting cognitive decline in an individual in need thereof, comprising administering to the individual an effective amount of a polypeptide that comprises a klotho KL1 domain, wherein the KL1 domain includes the beta-glucosidase/6-phospho-beta-glucosidase/beta-galactosidase motif that resides between amino acids 62-497 of SEQ ID NO:1, with the proviso that the polypeptide is not a fusion protein that also contains a fibroblast growth factor (FGF),
wherein the administering is systemic or peripheral, thereby improving cognitive function or inhibiting cognitive decline in the individual.

3. A method for improving cognitive function or inhibiting cognitive decline in an individual in need thereof, comprising administering to the individual an effective amount of a polypeptide that comprises a klotho KL1 domain, wherein the KL1 domain has at least one and up to 5% altered, inserted or deleted amino acids compared with the amino acid sequence of the KL1 domain in SEQ. ID NO:1, with the proviso that the polypeptide is not a fusion protein that also contains a fibroblast growth factor (FGF),
wherein the administering is systemic or peripheral, thereby improving cognitive function or inhibiting cognitive decline in the individual.

4. The method of claim 1, wherein the polypeptide further includes an amino acid sequence that is at least 95% identical to the sequence of the KL2 domain contained in SEQ. ID NO:1.

5. The method of claim 1, further comprising testing the cognitive function of the individual after administering the polypeptide.

6. The method of claim 1, which improves motor function in the individual.

7. The method of claim 1, wherein the polypeptide comprises an extracellular portion of human klotho formed by enzymatic cleavage between the KL1 and KL2 domains.

8. The method of claim 7, wherein the polypeptide ends in the amino acid sequence shown in SEQ. ID NO:2.

9. The method of claim 1, wherein the polypeptide comprises a soluble splice variant of klotho.

10. The method of claim 9, wherein the polypeptide comprises the KL1 domain but not the KL2 domain of human klotho.

11. The method of claim 10, wherein the polypeptide ends in the amino acid sequence shown in SEQ. ID NO:3.

12. The method of claim 1, wherein the polypeptide is a fusion protein that also includes a sequence of up to 100 additional amino acids.

13. The method of claim 1, wherein the polypeptide has beta-glucuronidase activity.

14. The method of claim 1, wherein the polypeptide binds or promotes activity of FGF23.

15. The method of claim 1, wherein the polypeptide results in induction of c-fos or increased expression of GluN2B.

16. The method of claim 1, wherein the polypeptide suppresses wnt signaling, insulin signaling, or transforming growth factor beta-1 (TGF-β1) activity.

17. The method of claim 1, wherein the polypeptide is administered intravenously or subcutaneously.

18. The method of claim 1, wherein the individual has traumatic brain injury.

19. The method of claim 1, wherein the individual has schizophrenia.

20. The method of claim 1, wherein the individual has Alzheimer's disease, frontotemporal dementia, Lewy body dementia, or cognitive impairment consequent to stroke.

21. The method of claim 1, wherein the individual has Parkinson's disease.

* * * * *